(12) United States Patent
de Graaff et al.

(10) Patent No.: US 10,413,504 B2
(45) Date of Patent: Sep. 17, 2019

(54) INTRAVAGINAL RING DRUG DELIVERY SYSTEM

(71) Applicant: Merck Sharp & Dohme B.V., Haarlem (NL)

(72) Inventors: Wouter de Graaff, Sprang-Capelle (NL); Willy J. H. Verhoeven, Cuijk (NL)

(73) Assignee: Merck Sharp & Dohme Corp., Rahway, NJ (US)

( * ) Notice: Subject to any disclaimer, the term of this patent is extended or adjusted under 35 U.S.C. 154(b) by 209 days.

(21) Appl. No.: 14/560,494

(22) Filed: Dec. 4, 2014

(65) Prior Publication Data

US 2015/0157561 A1     Jun. 11, 2015

Related U.S. Application Data

(60) Provisional application No. 61/914,500, filed on Dec. 11, 2013.

(30) Foreign Application Priority Data

Dec. 12, 2013 (EP) ..................................... 13196737

(51) Int. Cl.
| | |
|---|---|
| A61K 9/00 | (2006.01) |
| A61K 9/48 | (2006.01) |
| A61K 47/32 | (2006.01) |
| A61K 31/565 | (2006.01) |
| A61K 31/569 | (2006.01) |

(52) U.S. Cl.
CPC .......... *A61K 9/0034* (2013.01); *A61K 9/0036* (2013.01); *A61K 9/4816* (2013.01); *A61K 31/565* (2013.01); *A61K 31/569* (2013.01); *A61K 47/32* (2013.01)

(58) Field of Classification Search
None
See application file for complete search history.

(56) References Cited

U.S. PATENT DOCUMENTS

| | | | |
|---|---|---|---|
| 3,545,439 A | 12/1970 | Duncan et al. | |
| 3,854,480 A | 12/1974 | Zaffaroni et al. | |
| 3,995,633 A | 12/1976 | Gougeon et al. | |
| 3,995,634 A | 12/1976 | Drobish et al. | |
| 4,237,885 A | 12/1980 | Wong et al. | |
| 4,292,965 A | 10/1981 | Nash et al. | |
| 4,596,576 A | 6/1986 | de Nijs | |
| 4,629,449 A | 12/1986 | Wong | |
| 4,666,702 A | 5/1987 | Junginger | |
| 5,840,771 A | 11/1998 | Oldham et al. | |
| 5,851,547 A | 12/1998 | Fujioka et al. | |
| 5,972,372 A | 10/1999 | Saleh et al. | |
| 5,989,581 A | 11/1999 | Groenewegen | |
| 6,544,546 B1 | 4/2003 | Groenewegen | |
| 6,579,533 B1 | 6/2003 | Tormala et al. | |
| 6,590,081 B1 | 7/2003 | Zhang | |
| 6,831,073 B1 | 12/2004 | Lanquetin et al. | |
| 6,906,049 B1 | 6/2005 | Paris et al. | |
| 7,749,987 B2 | 7/2010 | Paris et al. | |
| 8,481,079 B2 * | 7/2013 | De Graaff | A61K 9/0036 424/484 |
| 8,741,329 B2 * | 6/2014 | de Graaff | A61F 6/06 424/400 |
| 8,808,744 B2 * | 8/2014 | de Graaff | A61K 9/0036 424/484 |
| 8,858,977 B2 * | 10/2014 | Groenewegen | A61K 9/0036 424/422 |
| 8,900,615 B2 * | 12/2014 | Groenewegen | A61K 9/0036 424/422 |
| 2003/0007992 A1 | 1/2003 | Gibson et al. | |
| 2003/0059456 A1 | 3/2003 | Malcolm et al. | |
| 2004/0062804 A1 | 4/2004 | Lee et al. | |
| 2006/0252835 A1 | 11/2006 | Broquaire et al. | |
| 2006/0280771 A1 | 12/2006 | Groenewegn et al. | |
| 2006/0281721 A1 * | 12/2006 | Edwards | A61K 9/2018 514/170 |
| 2008/0242650 A1 | 10/2008 | Thomas | |

(Continued)

FOREIGN PATENT DOCUMENTS

| | | |
|---|---|---|
| CN | 1463762 A | 12/2003 |
| EP | 0050867 B1 | 1/1988 |

(Continued)

OTHER PUBLICATIONS

Davies, G. C. et al, Ovarian Activity and Bleeding Patterns During Extended Continuous Use of a Combined Contraceptive Vaginal Ring, Contraception, 1992, p. 269-278, vol. 46.

Davies, G. C. et al, The Effects of a Combined Contraceptive Vaginal Ring Releasing Ethinyloestradiol and 3-Ketodesogestrel on Vaginal Flora, Contraception, 1992, p. 511-518, vol. 45.

Di Fabio, S. et al, Inhibition of vaginal transmission of HIV-1 in hu-SCID mice by the non-nucleoside reverse transcriptase inhibitor TMC120 in a gel formulation, AIDS, 2003, p. 1597-1604, vol. 17.

Keskar, V. et al, Cervical cancer treatment with a locally insertable controlled release delivery system, Journal of Controlled Release, 2006, p. 280-288, vol. 115.

(Continued)

*Primary Examiner* — Patricia Duffy
*Assistant Examiner* — Garen Gotfredson
(74) *Attorney, Agent, or Firm* — Janet E. Fair; Catherine D. Fitch

(57) ABSTRACT

Described herein is an intra-vaginal drug delivery system comprising (i) a core comprising a first thermoplastic polymer and a first therapeutic agent, wherein the first therapeutic agent is dissolved in the first thermoplastic polymer, and (ii) a skin surrounding the core comprising a second thermoplastic polymer, wherein the first therapeutic agent is less permeable in the second thermoplastic polymer than the first thermoplastic polymer, and a second therapeutic agent in solid form, wherein the second therapeutic agent is loaded in a portion of the skin.

8 Claims, 9 Drawing Sheets

(56) References Cited

U.S. PATENT DOCUMENTS

| | | |
|---|---|---|
| 2009/0142313 A1 | 6/2009 | Tailing et al. |
| 2010/0136090 A1 | 6/2010 | Driancourt et al. |
| 2012/0148655 A1 | 6/2012 | Variano et al. |

FOREIGN PATENT DOCUMENTS

| | | |
|---|---|---|
| EP | 0279982 A1 | 8/1988 |
| EP | 0303306 B1 | 3/1993 |
| EP | 0876815 B1 | 1/2002 |
| WO | WO1989009066 A1 | 10/1989 |
| WO | WO1997002015 A1 | 1/1997 |
| WO | WO1999030976 A1 | 6/1999 |
| WO | WO2003017971 A1 | 3/2003 |
| WO | WO2004103336 A2 | 12/2004 |
| WO | WO2005004837 A1 | 1/2005 |
| WO | WO2005089723 A1 | 9/2005 |
| WO | WO2007001888 A2 | 1/2007 |
| WO | 2008061963 A2 | 5/2008 |
| WO | WO2008100876 A1 | 8/2008 |
| WO | WO2009035562 A2 | 3/2009 |
| WO | WO2009036999 A1 | 3/2009 |
| WO | WO2009066006 A1 | 5/2009 |
| WO | WO2011011099 A1 | 1/2011 |
| WO | WO2012080195 A2 | 6/2012 |
| WO | WO2013120888 A2 | 8/2013 |
| WO | WO2015086491 A1 | 6/2015 |

OTHER PUBLICATIONS

Kim. H. et al, Application of Binary Polymer System in Drug Release Rate Modulation. 2. Influence of Formulation Variables and Hydrodynamic Conditions on Release Kinetics, Journal of Pharmaceutical Sciences, 1997, p. 323-328, vol. 86, No. 3.

Kubba, A. et al., Contraception, The Lancet, 2000, p. 1913-1919, vol. 356.

Ladipo, O. et al, Contraceptive implants, Current Opinion in Obstetrics and Gynecology, 1994, p. 564-569, vol. 6.

Madan, R. P. et al, Prioritizing prevention of HIV and sexually transmitted infections: first-generation vaginal microbicides, Curr Opin Infect Dis, 2006, p. 49-54, vol. 19.

Malcolm, K. et al., In vitro release of nonoxynol-9 from silicone matrix intravaginal rings, Journal of Controlled Release, 2003, p. 355-364, vol. 91.

Nascimento, M. D. L. P. et al, Nomegestrol acetate contraceptive implant use by women with sickle cell disease, Clin Pharmacol Ther, 1998, p. 433-438, vol. 64.

Skoler-Karpoff, S. et al, Efficacy of Carraguard for prevention of HIV infection in women in South Africa: a randomised, double-blind, placebo-controlled trial, The Lancet, 2008, p. 1977-1987, vol. 372.

Van Damme, L. et al, Lack of Effectiveness of Cellulose Sulfate Gel for the Prevention of Vaginal HIV Transmission, The New England Journal of Medicine, 2008, p. 463-472, vol. 359.

Van Laarhoven, J.A.H. et al, Effect of supersaturation and crystallization phenomena on the release properties of a controlled release device based on EVA copolymer, Journal of Controlled Release, 2002, p. 309-317, vol. 82.

Van Laarhoven, J.A.H., et al., In vitro release properties of etonogestrel and ethinyl estradiol from a contraceptive vaginal ring, International Journal of Pharmaceutics, 2002, p. 163-173, vol. 232.

Woolfson, A.D. et al, Design of a silicone reservoir intravaginal ring for the delivery of oxybutynin, Journal of Controlled Release, 2003, p. 465-476, vol. 91.

Woolfson, A.D. et al., Design of an intravaginal ring for the controlled delivery of 17B-estradiol as its 3-acetate ester, Journal of Controlled Release, 1999, p. 319-328, vol. 61.

Zaneveld, L. J. D. et al., Use of mandelic acid condensation polymer (SAMMA), a new antimicrobial contraceptive agent, for vaginal prophylaxis, Fertility and Sterility, 2002, p. 1107-1115, vol. 78, No. 5.

\* cited by examiner

INTRAVAGINAL RING DRUG DELIVERY SYSTEM

CROSS-REFERENCE TO RELATED APPLICATIONS

This application claims the benefit of priority under 35 U.S.C. 119 of U.S. Provisional Application Ser. No. 61/914,500, filed Dec. 11, 2013, and European Patent Application No. 13196737.4, filed Dec. 12, 2014, which are incorporated herein by reference in their entireties for all purposes.

FIELD OF THE INVENTION

The present invention relates to the field of female contraception. More particularly, the present invention relates to an intra-vaginal ring drug delivery system, for the simultaneous release of two or more active substances in a substantially constant ratio over a prolonged period of time.

BACKGROUND

Simultaneous drug release of two or more therapeutic agents from an intra-vaginal ring (IVR) drug delivery system is challenging because two or more drugs have to be released from one device and a multiple set of pre-defined drug release criteria must be fulfilled in order for the system to be effective. Several different IVR designs have attempted to provide specific controlled release solutions, few have been successful. Most, if not all, of the current IVRs, including those described in the patents and patent applications discussed below, suffer from at least one of the following drawbacks: lack of stability upon storage and transport, inability to independently adjust the release rate of multiple therapeutic components, difficulty or expense in manufacturing, inability to meet necessary release criteria to achieve the desired therapeutic effect.

Examples of known IVRs are described in U.S. Pat. Nos. 3,995,633; 3,995,634; 4,237,885; European patent publication 0,050,867; U.S. Pat. Nos. 4,292,965; 4,596,576; PCT publication WO 97/02015; European Patent 876 815; PCT publication WO2009/036999 and PCT publication WO2004/103336.

Specifically, WO2004/103336 discloses a drug delivery system comprising at least one compartment consisting of (i) a drug-loaded thermoplastic polymer core, (ii) a drug-loaded thermoplastic polymer intermediate layer and (iii) a non-medicated thermoplastic polymer skin covering the intermediate layer, wherein said intermediate layer is loaded with (a) crystals of a first pharmaceutically active compound and with (b) a second pharmaceutically active compound in dissolved form and wherein said core is loaded with said second compound in dissolved form.

Although the system disclosed in WO2004/103336 is suitable for the independent release of many drug combinations, the latter can still be improved upon. All the examples exemplified in WO2004/103336 include a diffusion path through a skin which is identical for all drugs, which are loaded in the skin-enclosed reservoir. The release of the crystalline drug and the dissolved drug loaded in the reservoir is governed by the same skin; hence, by varying skin properties the release of the crystalline drug and the dissolved drug will be tuned in the same direction—both up or both down—and the ratio in which these drugs are released remains essentially unaffected. In the WO2004/103336 delivery system the skin thickness is set to adjust the release of the crystalline drug to the desired level.

Additionally, the IVRs exemplified in WO2004/103336 suffer from the further limitation that the release of the dissolved drug is tuned to its desired rate by dissolving the proper amount in the reservoir. It appears that this specific amount, resulting in the exact concentration needed to obtain the desired release, is directly proportional to the saturation solubility and inversely proportional to the release rate of the crystalline drug. From a mechanistic point of view this is straightforward; low saturation solubility means a small driving force for diffusion and hence higher release rates for the crystalline drug can only be achieved if thin skins are applied. The release of the dissolved drug depends on the amount dissolved and on the thickness of the skin. If the same target release rate for the dissolved drug is to be matched with a thinner skin, less of drug should be dissolved in the core. So, the flipside of applying skins which are too thin is that the amount of dissolved drug becomes too small resulting in early depletion and steeply declining release profiles hampering broad application of the concept disclosed in WO2004/103336.

These phenomena can also be explained mathematically. The steady state drug release rate for cylindrical reservoir systems can be described mathematically by:

$$\frac{dM}{dt} = \frac{2\pi L D \Delta C}{\ln\left(\frac{r_0}{r_i}\right)} \quad (1)$$

in which:
dM/dt is the release rate [kg/s]
L is the length of the cylinder [m]
$r_0$ is outer radius of the skin [m]
$r_i$ is the inner radius of the skin [m]
D is the drug in polymer diffusion coefficient [m$^2$/s]
ΔC is the concentration gradient over the skin [kg/m$^3$]
DΔC Is drug permeability [kg/m·s]
For thin layers equation (1) can be approximated by:

$$\frac{dM}{dt} = \frac{2\pi L D \Delta C}{d} \quad (2)$$

in which "d" is the skin thickness [m]
From equation (2) it follows that the skin thickness is proportional with the drug permeability (DΔC) and inversely proportional to drug release (dM/dt) rate:

$$d \propto \frac{D \Delta C}{\frac{dM}{dt}} \quad (3)$$

Under sink conditions the concentration at the skin surface (r=r$_0$) approaches zero and equation (3) reduces to:

$$d \propto \frac{D \cdot C}{\frac{dM}{dt}}, \quad (4)$$

where C is the concentration in the skin at the interface (r=r$_i$)
In WO2004/103336 the crystalline drug in the intermediate layer and the dissolved drug loaded in core and intermediate layer pass through the same skin, hence the following condition (5) holds:

$$d \propto \frac{D_B \cdot C_B}{\frac{dM_B}{dt}} = \frac{D_A \cdot C_{A,s}}{\frac{dM_A}{dt}} \quad (5)$$

in which;
$dM_A/dt$ The release rate of the crystalline drug (A)
$dM_B/dt$ The release rate of the dissolved drug (B)
d Skin thickness
$D_A$ Diffusion coefficient of the crystalline drug (A)
$D_B$ Diffusion coefficient of drug (B)
$C_B$ The concentration of the completely dissolved drug
$C_{A,s}$ Saturation concentration of the crystalline drug
From equation (5) follows the required concentration of the dissolved drug (B):

$$C_B = \frac{\frac{dM_B}{dt}}{\frac{dM_A}{dt}} \times \frac{D_A}{D_B} \times C_{A,s} \quad (6)$$

Based on mechanistic considerations it can be concluded that the concentration of the dissolved drug ($C_B$) needed to obtain the right release for drug B, may become critically low when the saturation solubility of the crystalline drug ($C_{A,s}$) is relatively low and the target release rate ($dM_A/dt$) relatively high. Equation (6) indicates that concentration of dissolved drug ($C_B$) in the reservoir proportionally depends on the saturation solubility and inversely on the release rate of the crystalline drug ($dM_A/dt$). Hence $C_B$ decreases with decreasing saturation solubility $C_{A,s}$ and increasing release rate $dM_A/dt$ of the crystalline drug A. The drug-in-polymer diffusion coefficients in equation 6 are an intrinsic property of the polymer-drug pairs and hence these parameters may only coincidentally help to move $C_B$ in a higher direction. It can be concluded that $C_B$ and hence the amount of dissolved drug B in the delivery system, is tied by the solubility and release rate of drug A. Obviously if the amount of drug B dissolved in the reservoir is below a certain level, the release cannot be sustained over the intended duration of use. The IVRs described below are designed to overcome this and other limitations discussed above.

SUMMARY

The key difference between the present invention and previously exemplified IVR drug delivery systems, in particularly WO2004/103336, is that the IVR drug delivery systems described herein include a therapeutic agent in the skin, thus the average diffusion distance of the second therapeutic agent through the skin is less than the average diffusion distance of the therapeutic agents loaded in the core. In other words, the two therapeutic agents in WO2004/103336 are both required to pass completely through a rate limiting skin wherein only one of the two actives in the described IVR drug delivery systems passes entirely through a rate limiting skin, while the other passes partially through the rate limiting skin.

Described herein are IVR drug delivery systems comprising (i) a core comprising a first thermoplastic polymer and a first therapeutic agent, wherein the first therapeutic agent is dissolved in the first thermoplastic polymer, and (ii) a skin surrounding the core comprising a second thermoplastic polymer, wherein the first therapeutic agent is less permeable in the second thermoplastic polymer than the first thermoplastic polymer, and a second therapeutic agent in solid form, wherein the second therapeutic agent is loaded in a portion of the skin.

DETAILED DESCRIPTION

Figure 1:
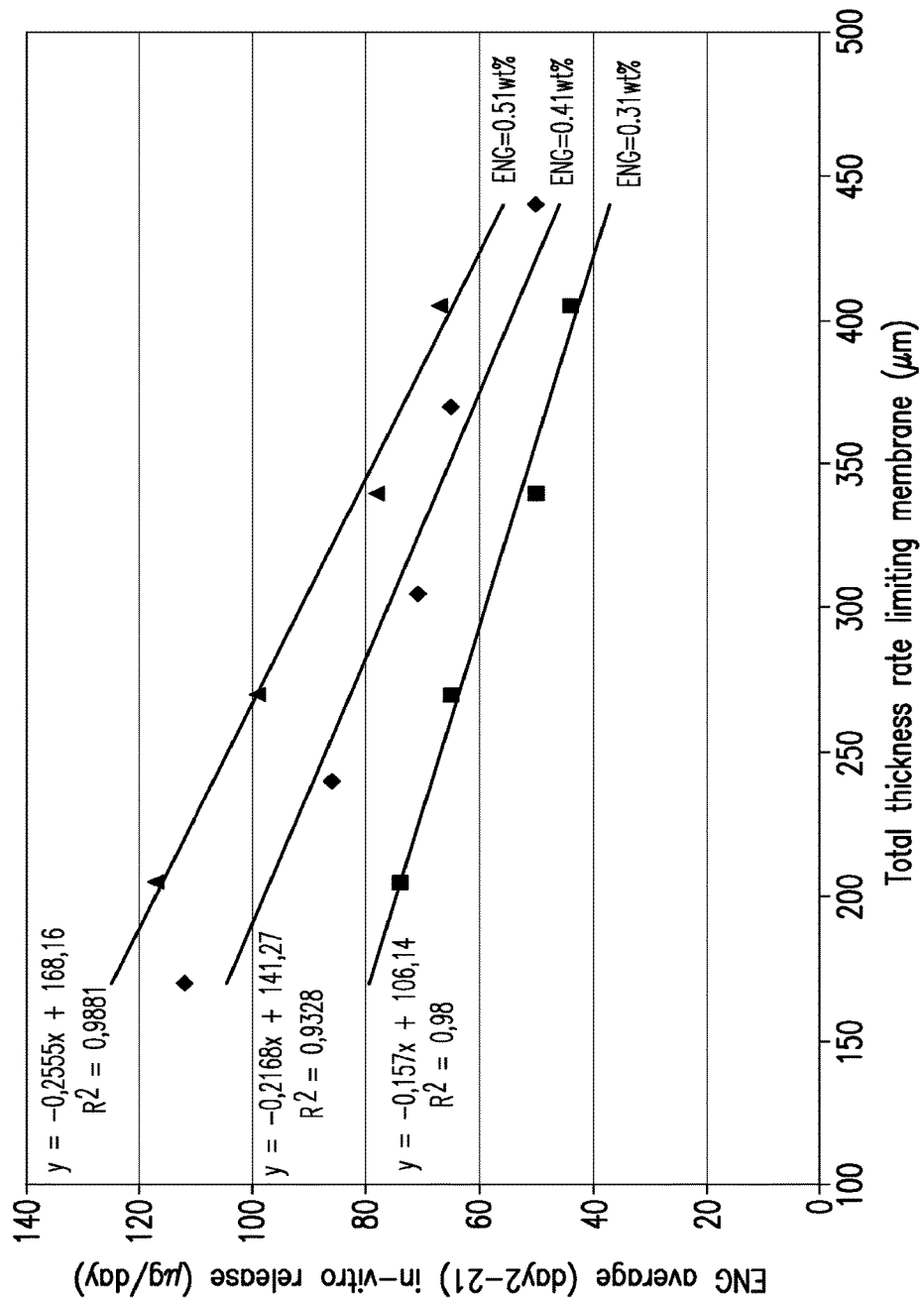
FIG. 1 shows the average etonogestrel (ENG) in-vitro release as a function of total skin thickness.

The following definitions are used in the subsequent further description of the invention:

"Drug", "medicament", "active agent" and "therapeutic agent" are used herein interchangeably.

"17beta-estradiol", "estradiol" and "E2" are used herein interchangeably.

"ENG" and "etonogestrel" are used herein interchangeably.

"EVA" and ethylene-vinylacetate are used herein interchangeably.

"Loaded" means the placement of the therapeutic agent in the drug delivery systems described herein upon manufacture.

"Matrix system" is defined as a system wherein a therapeutic agent is uniformly distributed in the matrix material and has no other release barrier than diffusion out of the matrix material.

"Permeable" means the measurement of a therapeutic agent's ability to pass through a thermoplastic polymer.

"Reservoir system" means a drug delivery system which includes a drug-loaded reservoir surrounded by a skin and the diffusion of the drug through the skin is rate limiting. As a result of the rate limiting properties of the skin, a spatially uniform concentration of dissolved drug will be maintained in the core during release; whereas a concentration gradient will develop primarily in the skin.

"Reservoir" is the interior part of the drug delivery system comprising of polymer(s) with relatively high permeability for the therapeutic agents.

"Rate limiting skin" is the part of the system which comprises polymer(s) with relatively low permeability for the therapeutic agents.

"VA" and "vinyl acetate" are used herein interchangeably.

Described herein are intra-vaginal drug delivery systems comprising (i) a core comprising a first thermoplastic polymer and a first therapeutic agent, wherein the first therapeutic agent is dissolved in the first thermoplastic polymer, and (ii) a skin surrounding the core comprising a second thermoplastic polymer, wherein the first therapeutic agent is less permeable in the second thermoplastic polymer than the first thermoplastic polymer, and a second therapeutic agent in solid form, wherein the second therapeutic agent is loaded in a portion of the skin.

IVR drug delivery systems described herein comprising the first therapeutic agent in the core and the second therapeutic agent in the skin, can be described as a hybrid between a reservoir type system and a matrix system or alternatively an enhanced matrix-type system. The therapeutic agent loaded in the core will behave like a reservoir type system and will be released in a near zero order fashion typical for reservoir systems, while the therapeutic agent loaded in the rate limiting skin will exhibit a release profile more akin to a matrix-type system. It is this hybrid configuration that allows the described IVR drug delivery systems to meet the necessary release criteria needed to achieve the desired therapeutic effect.

In a typical matrix-type system there is no rate limiting skin. Hence, beyond diffusion through the matrix polymer, there is no additional barrier impairing release. The drawback to the matrix system is that as the therapeutic agent nearest to the surface of the matrix system is released, a depletion layer is created and as more drug is released, the depletion layer will grow and move inwards over time. Eventually, a concentration gradient will build over the gradually increasing depletion layer resulting in an attenuated release profile typical for a solid therapeutic agent loaded polymer matrix.

The inventors have also found that the matrix component of the hybrid system can be improved by loading the therapeutic agent in the skin in such a way that a depletion layer is pre-formed or built-in, the drug loaded in the skin displays a near zero order release profile while obtaining higher release rates compared to a reservoir-type system. Thus, the IVR drug delivery systems described herein comprise a second therapeutic agent loaded in a portion of the skin. Upon manufacture, the second therapeutic agent is loaded in a portion of the skin, creating a built-in depletion layer, and not completely dispersed throughout the entire skin.

For example in certain embodiments of the IVR drug delivery system described herein, the skin has an inner portion adjacent to the core and an outer portion adjacent to the inner portion. In certain embodiments, the inner portion is loaded with the second therapeutic agent and the outer portion acts as the depletion layer.

The depletion layer of the IVR drug delivery system described herein allows the therapeutic agent in the skin to exhibit a near zero-order release profile while allowing the therapeutic agent in the skin to meet the necessary release criteria needed to achieve a desired therapeutic effect. Specifically, the therapeutic agent in the skin will be released at a higher dose as compared to a therapeutic agent release system wherein that same therapeutic agent had to pass through the entire skin. The reason for this may be attributed to the fact that the drug incorporated in the skin only passes through the depletion layer instead of through the entire skin. Hence, the diffusion length is largely reduced but not entirely absent.

In certain embodiments, the inner and outer portion of the skin is made from the same polymer. However, it can be envisioned that different polymers can be used for the inner and outer portion of the skin so long as the therapeutic agent in the skin experiences a reduced permeation resistance as it is being released and meets the necessary release criteria needed to achieve a desired therapeutic effect. Also it is important that the therapeutic agent in the core is less soluble in the polymers that make up the inner and outer portion of the skin as compared to the polymer in the core.

In certain embodiments, the skin comprises three portions, an inner portion adjacent to the core, an intermediate portion adjacent to the inner portion and an outer portion adjacent to the intermediate portion wherein, the intermediate portion is loaded with the second therapeutic agent and the outer portion acts as the depletion layer.

In certain embodiments, the inner, the intermediate and outer portions of the skin are made from the same polymer. However, it can be envisioned that different polymers can be used for the inner, intermediate and outer portions of the skin so long as the therapeutic agent in the skin experiences a reduced permeation resistance as it is being released and meets the necessary release criteria needed to achieve a desired therapeutic effect. Also it is important that the therapeutic agent in the core is less soluble in the polymers that make up the inner, the intermediate and outer portions of the skin than the polymer of the core.

In certain embodiments, the first therapeutic agent is in dissolved form in the core and the second therapeutic agent is in solid form in the skin. As used herein, solid can include crystalline or amorphous forms. In certain embodiments, the first therapeutic agent is in dissolved form in the core and the second therapeutic agent is in crystalline form in the skin. In certain embodiments, the first therapeutic agent is in dissolved form in the core and the second therapeutic agent is in amorphous form in the skin.

The thickness of the skin is determined by the concentration of the second therapeutic agent and the desired release rate of the second therapeutic agent. Suitable thicknesses of the skin can range from 40-700 µm, from 100-500 µm, from 100-450 µm, from 150-450 µm, from 175-400 µm, from 225-350 µm and from 225-300 µm. In certain embodiments the thickness of the skin is 40 µm, 60 µm, 70 µm, 80 µm, 90 µm, 100 µm, 130 µm, 150 µm, 170 µm, 200 µm, 205 µm, 240 µm, 250 µm, 270 µm, 276 µm, 290 µm, 300 µm, 305 µm, 340 µm, 370 µm, 405 µm, 440 µm, 500 µm, 600 µm or 700 µm. In some embodiments, the thickness of the skin is 180 µm, 250 µm or 280 µm.

In particular embodiments, the thickness of the skin ranges from 75-500 µm, from 125-400 µm, from 125-350 µm, from 150-300 µm or from 150-225 µm. In certain embodiments the thickness of the skin is 188 µm, 263 µm or 303 µm.

In certain embodiments of the IVR drug delivery systems described herein, the skin has a pre-formed or built-in depletion layer. The depletion layer allows the second therapeutic agent in the rate controlling skin to achieve the desired near zero order release rate. In certain embodiments, the skin comprises an inner portion adjacent to the core and an outer portion adjacent to the inner portion, wherein the inner and outer portions are both the same thermoplastic polymer. In other embodiments, the skin comprises three portions, an inner portion adjacent to core, an intermediate portion adjacent to the inner portion, and an outer portion adjacent to the intermediate portion wherein, the intermediate portion is loaded with the second therapeutic agent and the outer portion acts as the depletion layer.

The combined thickness of the inner and outer portion of the skin is determined by the concentration of the first therapeutic agent and the desired dose. The thickness of the outer portion of the skin is determined by the physical and chemical properties of the second therapeutic agent and the desired dose. The thickness of the inner portion follows from the total skin thickness and the thickness of the outer portion. Suitable thicknesses of the inner portion of the skin can range from 50-600 µm, from 100-450 µm, from 125-400 µm, from 125-350 µm, from 125-300 µm, or from 125-275 µm. In certain embodiments the thickness of the inner portion of the skin is 80 µm, 120 µm, 140 µm, 145 µm, 153 µm, 155 µm, 190 µm, 212 µm, 217 µm, 230 µm, 240 µm, 243 µm, 260 µm, 270 µm, 290 µm, 310 µm or 340 µm.

Suitable thicknesses of the outer potion of the skin can range from 10-100 µm, from 10-20 µm, from 20-30 µm, from 30-40 µm, from 50-60 µm, from 60-70 µm, from 70-80 µm or from 90-100 µm. In certain embodiments the thickness of the outer portion of the skin is 18 µm, 20 µm, 24 µm, 27 µm, 28 µm, 30 µm, 33 µm, 39 µm, 50 µm, 65 µm or 100 µm.

In the IVR drug delivery systems described herein, the core and the skin comprise a thermoplastic polymer. The type of thermoplastic polymer will depend on the first and second therapeutic agents used and the desired dose.

Suitable thermoplastic polymers that can be used in the IVR drug delivery system, drug delivery devices described herein, may, in principle, be any thermoplastic polymer or elastomer material suitable for pharmaceutical use, such as low density polyethylene, ethylene-vinylacetate copolymers, polyurethanes and styrene-butadiene-styrene copolymers. In certain embodiments, ethylene-vinylacetate copolymer (poly-EVA) is used in the core and the skin due to its excellent mechanical and physical properties (e.g. solubility of the steroids in the material). The poly-EVA material may be used for the core, as well as the skin and can be any commercially available ethylene-vinylacetate copolymer, such as the products available under the trade names: ELVAX, EVATANE, LUPOLEN, MOVRITON, ULTRATHENE, ATEVA AND VESTYPAR.

In specific embodiments, the core and the skin are made out of a different polymer grade. By electing different polymer grades for the core and the skin, the rate of release of the first therapeutic agent in the core can be adjusted.

In certain embodiments, the first thermoplastic polymer is ethylene-vinylacetate copolymer. In other embodiments, the second thermoplastic polymer is ethylene-vinylacetate copolymer. In still other embodiments, the first thermoplastic polymer and the second thermoplastic polymer each comprise an ethylene-vinylacetate copolymer, wherein the first thermoplastic polymer has a higher vinylacetate content than the second thermoplastic polymer.

In general, solubility of therapeutic agents increases with increasing vinylacetate content. Thus, having a skin of ethylene-vinylacetate copolymer with a lower vinylacetate content than the vinylacetate content of the core would enable the desired rate limiting properties of the skin. The permeability in EVA copolymers for small to medium sized drug molecules (M≤600 g/mol) is primarily determined by the vinylacetate (VA) to ethylene ratio. Low-VA content EVA copolymers are substantially less permeable than high VA-content copolymers and hence display desired rate limiting properties if used as skin. EVA copolymers with VA-content of 19% m/m or less (≤19% m/m) are substantially less permeable than EVA copolymers having VA-content above and including 25% m/m (≥25% m/m).

In some embodiments, the first thermoplastic polymer is an ethylene-vinylacetate copolymer and has a vinylacetate content of 25% or greater. In other embodiments, the first thermoplastic polymer has a vinylacetate content of greater than 25%. In still other embodiments, the first thermoplastic polymer has a vinylacetate content between 25-40% vinylacetate. In yet other embodiments, the first thermoplastic polymer has a vinylacetate content between 25-33% vinylacetate. In one embodiment, the first thermoplastic polymer has a vinylacetate content of 28%. In one embodiment, the first thermoplastic polymer has a vinylacetate content of 33%.

In some embodiments, the second thermoplastic polymer is an ethylene-vinylacetate copolymer and has a vinylacetate content of 19% or less. In other embodiments, the second thermoplastic polymer has a vinylacetate content of less than 19%. In still other embodiments, the second thermoplastic polymer has a vinylacetate content between 9-19% vinylacetate. In yet other embodiments, the second thermoplastic polymer has a vinylacetate content between 12-18% vinylacetate. In one embodiment, the second thermoplastic polymer has a vinylacetate content of 15%. In one embodiment, the second thermoplastic polymer has a vinylacetate content of 18%. In one embodiment, the second thermoplastic polymer has a vinylacetate content of 14.9% to 16.0%.

It should be noted that when a specific vinylacetate content e.g. 15% is mentioned it refers to the manufacture's target content and the actual vinylacetate content may vary from the target content by plus or minus 1% or 2%. The vinylacetate content refers to the vinylacetate content in the co-polymer determined by high resolution NMR. For determining the VA-content, 15-20 mg of sample is dissolved in tetrachloroethane-$d_2$ by heating for 15-18 hours at 100° C. A proton spectrum, accumulating 128 scans is acquired (at 90°–100° C.) with a recycle delay of 5 s. Signals from the —$CH_2$— moiety of vinyl and from the —CHOR-moiety are integrated to determine the VA-content. One of ordinary skill in the art would appreciate that suppliers may use internal analytical methods for determining vinylacetate content, thus there may be an off-set between methods.

In certain embodiments, the skin comprises an inner portion adjacent to the core and an outer portion adjacent to the inner portion, wherein the inner and outer portions are both the same thermoplastic polymer. In certain embodiments, suitable thermoplastic polymers for both the inner and outer portion of the skin are ethylene-vinylacetate copolymers. In certain embodiments, the ethylene-vinylacetate copolymer has a vinylacetate content of 19% or less. In certain embodiments, the ethylene-vinylacetate copolymer has a vinylacetate content between 9-19% vinylacetate. In certain embodiments, the ethylene-vinylacetate copolymer has a vinylacetate content between 12-18% vinylacetate. In one embodiment, the ethylene-vinylacetate copolymer has a vinylacetate content of 14.9% to 16.0%. In one embodiment, the ethylene-vinylacetate copolymer has a vinylacetate content of 15%. In one embodiment, the ethylene-vinylacetate copolymer has a vinylacetate content of 18%.

In certain embodiments, the skin comprises an inner portion adjacent to the core and an outer portion adjacent to the inner portion, wherein the inner and outer portions are each made of a different thermoplastic polymer. Different polymers for the inner and outer portion of the skin can be used so long as the second therapeutic agent in the skin experiences a reduced permeation resistance as it is being released and the released second therapeutic agent meets the necessary release criteria needed to achieve a desired therapeutic effect.

In certain embodiments, the inner portion of the skin comprises an ethylene-vinylacetate copolymer having a vinylacetate content of less than 19% vinylacetate. In certain embodiments, the inner portion of the skin comprises an ethylene-vinylacetate copolymer having a vinylacetate content between 9-19% vinylacetate. In certain embodiments, the inner portion of the skin comprises an ethylene-vinylacetate copolymer having a vinylacetate content between 12-18% vinylacetate. In one embodiment, the ethylene-vinylacetate copolymer of the inner portion of the skin has a vinylacetate content of 14.9%.-16.0%. In one embodiment, the ethylene-vinylacetate copolymer of the inner portion of the skin has a vinylacetate content of 15%. In one embodiment, the ethylene-vinylacetate copolymer of the inner portion of the skin has a vinylacetate content of 18%.

In certain embodiments, the outer portion of the skin comprises an ethylene-vinylacetate copolymer that has a higher vinylacetate content than the inner portion of the rate limiting skin. In certain embodiments, the outer portion of the skin comprises an ethylene-vinylacetate copolymer that has a lower vinylacetate content than the inner portion of the rate limiting skin. In certain embodiments the outer portion of the skin has a vinylacetate content between 9-19% vinylacetate. In certain embodiments, the outer portion of the skin comprises an ethylene-vinylacetate copolymer having a vinylacetate content between 12-18% vinylacetate. In one embodiment, the ethylene-vinylacetate copolymer of the outer portion of the skin has a vinylacetate content of 14.9%.-16.0%. In one embodiment, the ethylene-vinylacetate copolymer of the outer portion of the skin has a vinylacetate content of 15%. In one embodiment, the ethylene-vinylacetate copolymer of the outer portion of the skin has a vinylacetate content of 18%.

For example described herein is a IVR drug delivery system comprising (i) a core comprising an ethylene-vinylacetate copolymer having a vinylacetate content of greater than 25% and a first therapeutic agent, wherein the first therapeutic agent is dissolved in the first ethylene-vinylacetate copolymer, and (ii) a skin surrounding the core, wherein the skin comprises (a) an inner portion, wherein the inner portion comprises an ethylene-vinylacetate copolymer having a vinylacetate content including and between 9%-19% and a second therapeutic agent, wherein the second therapeutic agent is in crystalline form and (b) an outer portion comprising an ethylene-vinylacetate copolymer having a vinylacetate content including and between 9%-19%.

The IVR drug delivery systems described herein comprise at least two active drug substances. In certain embodiments described herein, the first therapeutic agent and the second therapeutic agent are steroids. However, non-steroidal therapeutic agents are also contemplated.

In certain embodiments the first therapeutic agent is a steroid. More specifically, in certain embodiments the first therapeutic agent is a progestogenic steroidal compound. Suitable progestogens include, but are not limited to, desogestrel, etonogestrel, levonorgestrel, norgestimate, gestodene or any other steroidal compound with progestogenic activity.

In certain embodiments the second therapeutic agent is a steroid. More specifically, in certain embodiments the second therapeutic agent is an estrogenic steroidal compound. Suitable estrogens include, but are not limited to, 17beta-estradiol, 17beta-estradiol hemi-hydrate, estriol, mestranol and ethinyl estradiol.

In certain embodiments of the IVR drug delivery systems described herein, the progestogen is etonogestrel. In a specific embodiment of the IVR drug delivery system described herein, the estrogen for contraceptive use is 17beta-estradiol or 17beta-estradiol hemi-hydrate. In another embodiment, 17beta-estradiol is the estrogen used for hormone replacement therapy.

In certain embodiments of the IVR drug delivery systems described herein, etonogestrel is present in the core at about 0.10%-1.0% by weight. In other embodiments, etonogestrel is present in the core at about 0.20-0.70% by weight, at about 0.30-0.60% by weight, at about 0.40-0.60% by weight, at about 0.40-0.55% by weight, or at about 0.31%, or 0.41 or 0.51% by weight.

The IVR drug delivery system described herein, is capable of releasing etonogestrel over a period of 21, 28 or 31 days at an average rate of between 25-200 µg per day. As discussed herein "average rate" of a therapeutic agent is the average rate of drug release over a certain time period and when the period of time is described by a number of days usually the release rate of the first day is excluded. In certain embodiments, the IVR drug delivery system described herein is capable of releasing etonogestrel at an average rate of between 50-175 µg per day. In certain embodiments, the IVR drug delivery system described herein is capable of releasing etonogestrel at an average rate of between 50-150 µg per day. In certain embodiments, the IVR drug delivery system described herein is capable of releasing etonogestrel at an average rate of between 75-125 µg per day.

The IVR drug delivery system described herein, in specific embodiments, is capable of releasing etonogestrel over a period of 21 days at an average rate of between 25-200 µg per day. In certain embodiments, the IVR drug delivery system described herein is capable of releasing etonogestrel over a period of 21 days at an average rate of between 50-175 µg per day. In certain embodiments, the IVR drug delivery system described herein is capable of releasing etonogestrel over a period of 21 days at an average rate of between 50-150 µg per day. In certain embodiments, the IVR drug delivery system described herein is capable of releasing etonogestrel over a period of 21 days at an average rate of between 75-125 µg per day.

The IVR drug delivery system described herein is capable of releasing etonogestrel over a period of one month at an average rate of between 25-200 µg per day. In certain embodiments, the IVR drug delivery system described herein is capable of releasing etonogestrel over a period of one month at an average rate of between 50-150 µg per day. In certain embodiments, the IVR drug delivery system described herein is capable of releasing etonogestrel over a period of one month at an average rate of between 50-125 µg per day. In certain embodiments, the IVR drug delivery system described herein is capable of releasing etonogestrel over a period of one month at an average rate of between 75-125 µg per day.

In certain embodiments, the IVR drug delivery system described herein is capable of releasing 17beta-estradiol over a period of 21, 28 or 31 days at an average rate of between 50-450 µg per day. In certain embodiments, the IVR drug delivery system described herein is capable of releasing 17beta-estradiol at an average rate of between 100-400 µg per day. In certain embodiments, the IVR drug delivery system described herein is capable of releasing 17beta-estradiol at an average rate of between 225-360 µg per day. In certain embodiments, the IVR drug delivery system described herein is capable of releasing 17beta-estradiol at an average rate of between 240-360 µg per day. In certain embodiments, the IVR drug delivery system described herein is capable of releasing 17beta-estradiol at an average rate of between 300-360 µg per day.

In certain embodiments, the IVR drug delivery system described herein is capable of releasing 17beta-estradiol over a period of 21 days at an average rate of between 50-450 µg per day. In certain embodiments, the IVR drug delivery system described herein is capable of releasing 17beta-estradiol over a period of 21 days at an average rate of between 100-400 µg per day. In certain embodiments, the IVR drug delivery system described herein is capable of releasing 17beta-estradiol over a period of 21 days at an average rate of between 225-360 µg per day. In certain embodiments, the IVR drug delivery system described herein is capable of releasing 17beta-estradiol over a period of 21 days at an average rate of between 240-360 µg per day. In certain embodiments, the IVR drug delivery system described herein is capable of releasing 17beta-estradiol over a period of 21 days at an average rate of between 300-360 µg per day.

In certain embodiments, the IVR drug delivery system described herein is capable of releasing 17beta-estradiol over a period of one month at an average rate of between 50-450 µg per day. In certain embodiments, the IVR drug delivery system described herein is capable of releasing 17beta-estradiol at an average rate of between 100-400 µg per day. In certain embodiments, the IVR drug delivery system described herein is capable of releasing 17beta-estradiol at an average rate of between 225-360 µg per day. In certain embodiments, the IVR drug delivery system described herein is capable of releasing 17beta-estradiol at an average rate of between 240-360 µg per day. In certain embodiments, the IVR drug delivery system described herein is capable of releasing 17beta-estradiol at an average rate of between 300-360 µg per day In certain embodiments, the IVR drug delivery system described herein is capable of releasing etonogestrel at an average rate of 25 µg per day. In certain embodiments, the IVR drug delivery system described herein is capable of releasing etonogestrel at an average rate of 50 µg per day. In certain embodiments, the IVR drug delivery system described herein is capable of releasing etonogestrel at an average rate of 75 µg per day. In certain embodiments, the IVR drug delivery system described herein is capable of releasing etonogestrel at an average rate of 100 µg per day. In certain embodiments, the IVR drug delivery system described herein is capable of releasing etonogestrel at an average rate of 125 µg per day. In certain embodiments, the IVR drug delivery system described herein is capable of releasing etonogestrel at an average rate of 150 µg per day. In certain embodiments, the IVR drug delivery system described herein is capable of releasing etonogestrel at an average rate of 200 µg per day.

In certain embodiments, the IVR drug delivery system described herein is capable of releasing 17beta-estradiol at an average rate of 50 µg per day. In certain embodiments, the IVR drug delivery system described herein is capable of releasing 17beta-estradiol at an average rate of 100 µg per day. In certain embodiments, the IVR drug delivery system described herein is capable of releasing 17beta-estradiol at an average rate of 150 µg per day In certain embodiments, the IVR drug delivery system described herein is capable of releasing 17beta-estradiol at an average rate of 200 µg per day. In certain embodiments, the IVR drug delivery system described herein is capable of releasing 17beta-estradiol at an average rate of 225 µg per day. In certain embodiments, the IVR drug delivery system described herein is capable of releasing 17beta-estradiol at an average rate of 240 µg per day. In certain embodiments, the IVR drug delivery system described herein is capable of releasing 17beta-estradiol at an average rate of 300 µg per day. In certain embodiments, the IVR drug delivery system described herein is capable of releasing 17beta-estradiol at an average rate of 360 µg per day. In certain embodiments, the IVR drug delivery system described herein is capable of releasing 17beta-estradiol at an average rate of 400 µg per day. In certain embodiments, the IVR drug delivery system described herein is capable of releasing 17beta-estradiol at an average rate of 450 µg per day In certain embodiments of the IVR drug delivery systems described herein, 17beta-estradiol is present in the in the skin at about 2.5-60% by weight. In other embodiments, 17beta-estradiol is present in the skin at about 9-50% by weight, at about 12-40% by weight, or at about 15-30% by weight. In certain embodiments, 17beta-estradiol is present in 9%, 12%, 15%, 18%, or 27%.

In certain embodiments, the IVR drug delivery system described herein comprises (i) a core comprising ethylene-vinylacetate copolymer with 28% vinylacetate content and etonogestrel, wherein the etonogestrel is dissolved in the ethylene-vinylacetate copolymer, and (ii) a skin surrounding the core comprising an ethylene-vinylacetate copolymer having 15% vinylacetate content and 17beta-estradiol, wherein the 17beta-estradiol is in crystalline form. Such a ring is capable of releasing the etonogestrel in an amount of 75 µg, 100 µg or 125 µg per day and 17beta-estradiol in the amount of 300 µg per day. Comparably, single compartment IVR drug delivery systems in the prior art are not capable of releasing such high levels of 17beta-estradiol and at the same time achieving controlled sustained release of etonogestrel in the desired therapeutic range while being stable at room temperature due to the existence of a rate limiting skin or other limiting feature.

The IVR drug delivery systems described herein can be manufactured in any size as required. In one embodiment, the ring has an outer diameter (outer circumference) of between 50 and 60 mm and in another embodiment between 52 and 56 mm; the cross sectional diameter is between about 2.5 and 6 mm, in a specific embodiment between about 3.0 and 5 mm, and in another embodiment between about 3.5 and 4.5 mm and in yet another embodiment is 4.0 mm.

In certain embodiments of the IVR drug delivery systems described herein, the surface of the core body is more than 800 mm$^2$, and in another embodiment more than 1000 mm$^2$ and will typically be in the order of 1700-2200 mm$^2$, though significantly larger surfaces are possible, provided that the design (physical dimensions) of the IVR drug delivery system prevents inconvenience for the subject. It may sometimes be required to add a second compartment which is a placebo compartment or a compartment loaded with one or more other drugs. Such an extra compartment may be necessary for example in practising hormonal replacement therapy, where the ratio between progestogen and estrogen is different from the ratio suitable for contraception. Such an extra compartment can also be necessary to administer, in addition to the steroids, anti-microbial drugs to treat and/or prevent STD's such as AIDS, chlamydia, herpes and gonorrhea.

Also described herein are IVR drug delivery systems in which the inner portion of the skin or the core, in addition to steroids for contraception or hormone replacement, also comprises anti-microbials, e.g. to concomitantly treat and/or prevent sexually-transmitted diseases (STD's) such as HIV, herpes, chlamydia and gonorrhea.

Any anti-microbial drug can be incorporated into an IVR drug delivery system described herein (in the inner portion of the skin and/or in the core and/or in an additional compartment). The anti-microbial drug can be any anti-bacterial drug such as any antibiotic, any anti-viral agent, any anti-fungal agent or any anti-protozoal agent. An example of an anti-microbial drug contemplated to be incorporated into the IVR drug delivery systems described herein is mandelic acid condensation polymer (Zanefeld et al. (2002), *Fertility and Sterility* 78(5): 1107-1115). Another example is dapivirine (4-[[4-[2,4,6-trimethylphenyl)amino-2-pyrimidinyl]amino]benzonitrile).

Additionally, the IVR drug delivery system described herein is stable at room temperature. As used herein, "room temperature" lies anywhere between about 18° C. and about 30° C. As used herein, a physically stable drug delivery system (ring) is a system which can be stored at about 18° C.-30° C. for at least about one and a half (1.5) years.

The IVR drug delivery system described herein is primarily designed for contraceptive use, but may also be used under certain conditions in hormonal replacement therapy.

The IVR drug delivery system described herein may also be used to concomitantly provide contraception and combat microbial disease. The microbial infection to be treated and/or prevented can be any bacterial, viral, fungal or protozoal infection. Specifically, sexually transmitted diseases such as HIV, chlamydia, gonorrhea, or herpes may be treated by incorporation of an anti-microbial agent into the IVR drug delivery systems described herein.

Also described herein is a method of contraception which comprises the steps of positioning a IVR drug delivery system described herein within the female vaginal tract and retaining the system within the vaginal tract for at least approximately 21 days.

Also described herein is a method of concomitantly providing contraception and treating or preventing a sexually transmitted disease which comprises the steps of positioning a IVR drug delivery system drug delivery system described herein within the female vaginal tract and retaining the system within the vaginal tract for at least approximately 21 days.

In one embodiment, the drug delivery system is removed after about 21 days for an approximate one week period to permit menstruation. After the approximate week to allow for menstruation, a new IVR drug delivery system drug delivery system described herein is inserted into the female vagina to provide contraception in the next female cycle or cycles.

Also described herein is a use of an IVR drug delivery system described herein for the manufacture of a contraceptive kit.

Also described herein is a use of an IVR drug delivery system described herein for the manufacture of a medicament for hormone replacement therapy.

Also described herein is a use of an IVR drug delivery system described herein for the manufacture of a medicament for dysmenorrhea.

Also described herein is a use of an IVR drug delivery system described herein for the manufacture of a combination preparation to provide contraception and to treat and/or prevent a sexually transmitted disease such as for example AIDS, herpes, chlamydia and gonorrhea.

Also described herein is a method of manufacturing the IVR drug delivery system described herein:
(i) Producing a polymer core granulate comprising a first therapeutic agent;
(ii) producing a polymer inner portion of the skin granulate comprising the second therapeutic agent;
(iii) producing a polymer outer portion of the skin granulate; and
(iv) co-extruding three granulates, the core granulate, the granulate for the inner portion of the skin and the granulate for the outer portion of the skin, to form the three-layered drug delivery system.

The production of the polymer core granulate and polymer inner portion of the skin granulate comprises:
(a) grinding the polymer;
(b) dry powder mixing at least a portion of the ground polymer with the therapeutic agent(s) to be loaded in the inner portion of the skin;
(c) dry powder mixing at least a portion of the ground polymer with the therapeutic agent(s) to be loaded in the core;
(d) blend extruding the resulting powder mixtures of steps (b) and (c);
(e) cutting the resulting polymer strands into granules, thereby obtaining a core granulate and an inner portion of the skin granulate;
(f) lubricating both core granulate and inner portion of the skin with a lubricant; wherein steps (b) and (c) are interchangeable.

Examples of embodiments are further described in the following examples which are not in any way intended to limit the scope of the invention as claimed.

EXAMPLES

In the following examples the following acronyms are used:
ENG=etonogestrel
E2=estradiol
EVA32 ethylene-vinylacetate
VA=vinylacetate Example 1

Preparation of Vaginal Drug Delivery Systems

Mixing Therapeutic Agents Through the Copolymers EVA15, EVA18 and EVA28

The active ingredients etonogestrel (ENG) and 17beta-estradiol (E2) were homogeneously mixed through the polymer and for this purpose two subsequent mixing steps have been performed. In the first step, dry powder mixing was performed with the micronized therapeutic agents and polymer powder. These micronized agents were mixed with polymer powder in a stainless steel drum using a Rhönrad mixer (Barrel-hoop principle) with a fixed rotation speed of approximately 26 or 45 rpm for 60 minutes. Subsequently the homogenized powder mixtures were blend extruded using a 25 mm co-rotating double screw blend extruder (Berstorff ZE25) and the resulting medicated polymer strands were cut into granules using a Scheer granulator. Mixtures A, B, C, D and E, comprising EVA15, and mixtures F, G, H and I, comprising EVA18, were blend extruded at 100° C. and 95° C. respectively. Mixtures J, K, and L, comprising EVA28 were blend extruded at 85° C. Mixture M, comprising EVA28, was blend extruded at 110° C. After granulation these batches were lubricated with magnesium stearate in order to facilitate the next processing step (co-extrusion).

Mixing Therapeutic Agents Through the Copolymers EVA15 and EVA28

The active ingredients etonogestrel (ENG) and 17beta-estradiol (E2) were homogeneously mixed through the polymer and for this purpose two subsequent mixing steps have been performed. In the first step, dry powder mixing was performed with the micronized therapeutic agents and polymer powder. These micronized agents were mixed with polymer powder in a stainless steel bin blender with a fixed rotation speed of approximately 6 rpm for 60 minutes. Subsequently the homogenized powder mixtures were blend extruded using a 50 mm co-rotating double screw blend extruder (Berstorff ZE50) and the resulting medicated polymer strands were cut into granules using a Scheer granulator. Mixture D, comprising EVA15, and mixtures K and L, comprising EVA28, were blend extruded at 110° C. After granulation these batches were lubricated with magnesium stearate in order to facilitate the next processing step (co-extrusion).

The active granule composition comprising either EVA15 or EVA18 skin copolymer and E2 is given in Table $1^a$ and $1^b$.

TABLE $1^a$

Composition E2 Granulate in EVA15

| Material | Active granulate A | Active granulate B | Active granulate C | Active granulate D | Active granulate E |
|---|---|---|---|---|---|
| Estradiol | 9 wt % | 12 wt % | 15 wt % | 18 wt % | 27 wt % |
| EVA 15 | 90.9 wt % | 87.9 wt % | 84.9 wt % | 81.9 wt % | 72.9 wt % |
| Magnesium stearate | 0.1 wt % | 0.1 wt % | 0.1 wt % | 0.1 wt % | 0.1 wt % |
| Total | 100.0 wt % | 100.0 wt % | 100.0 wt % | 100.0 wt % | 100.0 wt % |

TABLE $1^b$

Composition E2 Medicated Granulate in EVA18

| Material | Active granulate F | Active granulate G | Active granulate H | Active granulate I |
|---|---|---|---|---|
| Estradiol | 9 wt % | 12 wt % | 15 wt % | 18 wt % |
| EVA 18 | 90.9 wt % | 87.9 wt % | 84.9 wt % | 81.9 wt % |
| Magnesium stearate | 0.1 wt % | 0.1 wt % | 0.1 wt % | 0.1 wt % |
| Total | 100.0 wt % | 100.0 wt % | 100.0 wt % | 100.0 wt % |

The active granule composition comprising EVA28 core copolymer and ENG is given in Table 2.

TABLE 2

Composition ENG Medicated Granulate in EVA28

| Material | Active granulate J | Active granulate K | Active granulate L | Active granulate M |
|---|---|---|---|---|
| Etonogestrel | 0.31 wt % | 0.41 wt % | 0.51 wt % | 0.69 wt % |
| EVA 28 | 99.59 wt % | 99.49 wt % | 99.39 wt % | 99.21 wt % |
| Magnesium stearate | 0.1 wt % | 0.1 wt % | 0.1 wt % | 0.1 wt % |
| Total | 100.0 wt % | 100.0 wt % | 100.0 wt % | 100.0 wt % |

Tri-layer co-extrusion of Batches in Tables $3^a$, $3^b$, $3^c$ and $3^e$

The different granulates containing the active ingredients (either E2 or ENG) were further processed to drug loaded fibers by means of co-extrusion using a Fourne co-extruder. This co-extrusion set-up consisted of three coupled single screw extruders (25/18/18 mm) The 25 mm extruder processed the core and both 18 mm extruders processed the inner and outer portion of the skin. The three extruders, equipped with three separate spinning pumps to control the volume flow rates, were connected with an extruder-die in which the three melt flows were combined to form a fiber comprising of a core and a skin, the latter comprising of an inner and outer portion. A capillary of 2.7 mm was used. All fibers were extruded at an extrusion temperature of 105° C. The spinning rate was approximately 4.0 m/min to tune the desired fiber diameter of 4.0 mm. The desired layer thickness for skin and intermediate layer was obtained by adjustment of the spinning pump rates. Each of the tri-layer fiber variants were produced by using the appropriate spinning rate and spinning pump settings. After a start-up phase a certain length of fiber was collected on a need basis. In between batches, after re-setting of the spinning pump rates to the settings required for the next batch, the process was allowed to stabilize for 5 minutes before fiber collecting was resumed. In case of changing skin and/or core composition a purging step was performed. Purging consisted of displacing the hold-up volume in the extruder by 500 g of material with the composition required for production of the next batch and only after displacing the hold-up fiber collection was resumed. The outer diameter of the fiber was measured on-line continuously using a laser micrometer and recorded. The thickness of the inner portion and outer portion of the skin was controlled by means of the spinning pump settings.

The composition of different series of fiber batches produced are given in Tables $3^a$, $3^b$, $3^c$ and $3^e$.

Tri-Layer Co-Extrusion of Batches in Tables $3^d$

The different granulates containing the active ingredients (either E2 or ENG) were further processed to drug loaded fibers by means of co-extrusion using a double lines MTSA co-extruder. This co-extrusion set-up consisted of three coupled single screw extruders (35/22/18 mm) The 35 mm extruder processed the core, the 22 mm extruder processed the inner portion of the skin and the 18 mm extruder processed the outer portion of the skin. The three extruders, equipped with three separate spinning pumps per spinning line to control the volume flow rates, were connected with an extruder-die in which the three melt flows were combined to form a fiber comprising of a core and a skin, the latter comprising of an inner and outer portion. A capillary of 2.7 mm was used. All fibers were extruded at an extrusion temperature of 105° C. The spinning rate was approximately 4.0-6.5 m/min to tune the desired fiber diameter of 4.0 mm. The desired layer thickness for skin and intermediate layer was obtained by adjustment of the spinning pump rates. Each of the tri-layer fiber variants were produced by using the appropriate spinning rate and spinning pump settings. After a start-up phase a certain length of fiber was collected on a need basis. In between batches, after re-setting of the spinning pump rates to the settings required for the next batch, the process was allowed to stabilize for 5 minutes before fiber collecting was resumed. In case of changing skin and/or core composition a purging step was performed. Purging consisted of displacing the hold-up volume in the extruder by 1 kg (outer portion of skin), 1.5 kg (inner portion of skin) or 3 kg (core) of material with the composition required for production of the next batch and only after displacing the hold-up fiber collection was resumed. The outer diameter of the fiber was measured on-line continuously using a laser micrometer and recorded. The thickness of the inner portion and outer portion of the skin was controlled by means of the spinning pump settings.

The composition of different series of fiber batches produced are given in Table $3^d$.

TABLE $3^a$

Fiber dimension and characteristics of A-series rings

| | Outer skin portion | | Inner Skin Portion | | Reservoir | |
|---|---|---|---|---|---|---|
| Batch | Placebo Polymer | Thickness (μm) | Granulate E2 | wt % | Thickness (μm) | Granulate ENG | wt % |
| A1 | EVA15 | 100 | D | 18 | 140 | K | 0.41 |
| A2 | EVA15 | 65 | D | 18 | 340 | J | 0.31 |
| A3 | EVA15 | 100 | D | 18 | 240 | L | 0.51 |
| A4 | EVA15 | 30 | D | 18 | 140 | K | 0.41 |
| A5 | EVA15 | 65 | D | 18 | 240 | K | 0.41 |
| A6 | EVA15 | 65 | D | 18 | 240 | K | 0.41 |
| A7 | EVA15 | 100 | D | 18 | 340 | K | 0.41 |
| A8 | EVA15 | 30 | D | 18 | 240 | J | 0.31 |
| A9 | EVA15 | 65 | D | 18 | 340 | L | 0.51 |
| A10 | EVA15 | 65 | D | 18 | 140 | J | 0.31 |
| A11 | EVA15 | 65 | D | 18 | 240 | K | 0.41 |
| A12 | EVA15 | 100 | D | 18 | 240 | J | 0.31 |
| A13 | EVA15 | 65 | D | 18 | 140 | L | 0.51 |
| A14 | EVA15 | 30 | D | 18 | 240 | L | 0.51 |
| A15 | EVA15 | 30 | D | 18 | 340 | K | 0.41 |

TABLE $3^b$

Fiber dimension and characteristics of B-series rings

| | Outer skin portion | | Inner Skin Portion | | Reservoir | |
|---|---|---|---|---|---|---|
| Batch | Placebo Polymer | Thickness (μm) | Granulate E2 | wt % | Thickness (μm) | Granulate ENG | wt % |
| B1 | EVA15 | 65 | D | 18 | 140 | K | 0.41 |
| B2 | EVA15 | 65 | D | 18 | 340 | K | 0.41 |
| B3 | EVA15 | 65 | C | 15 | 140 | K | 0.41 |
| B4 | EVA15 | 65 | C | 15 | 340 | K | 0.41 |
| B5 | EVA15 | 65 | B | 12 | 140 | K | 0.41 |
| B6 | EVA15 | 65 | B | 12 | 340 | K | 0.41 |
| B7 | EVA15 | 65 | A | 9 | 140 | K | 0.41 |
| B8 | EVA15 | 65 | A | 9 | 340 | K | 0.41 |
| B9 | EVA18 | 65 | I | 18 | 140 | K | 0.41 |
| B10 | EVA18 | 65 | I | 18 | 340 | K | 0.41 |
| B11 | EVA18 | 65 | H | 15 | 140 | K | 0.41 |
| B12 | EVA18 | 65 | H | 15 | 340 | K | 0.41 |
| B13 | EVA18 | 65 | G | 12 | 140 | K | 0.41 |
| B14 | EVA18 | 65 | G | 12 | 340 | K | 0.41 |
| B15 | EVA18 | 65 | F | 9 | 140 | K | 0.41 |
| B16 | EVA18 | 65 | F | 9 | 340 | K | 0.41 |

TABLE $3^c$

Fiber dimension and characteristics of C-series rings

| | Outer skin portion | | Inner Skin Portion | | Reservoir | |
|---|---|---|---|---|---|---|
| Batch | Placebo Polymer | Thickness (μm) | Granulate E2 | wt % | Thickness (μm) | Granulate ENG | wt % |
| C1 | EVA15 | 50 | A | 9 | 190 | K | 0.41 |
| C2 | EVA15 | 50 | A | 9 | 290 | K | 0.41 |
| C3 | EVA15 | 50 | D | 18 | 240 | K | 0.41 |
| C4 | EVA15 | 50 | D | 18 | 240 | K | 0.41 |
| C5 | EVA15 | 50 | E | 27 | 190 | K | 0.41 |
| C6 | EVA15 | 50 | A | 9 | 290 | K | 0.41 |
| C7 | EVA15 | 50 | E | 27 | 290 | K | 0.41 |
| C8 | EVA15 | 50 | E | 27 | 190 | K | 0.41 |
| C9 | EVA15 | 50 | A | 9 | 190 | K | 0.41 |
| C10 | EVA15 | 50 | E | 27 | 290 | K | 0.41 |
| C11 | EVA15 | 50 | D | 18 | 240 | K | 0.41 |
| C12 | EVA15 | 50 | D | 18 | 80 | K | 0.41 |

TABLE $3^d$

Fiber dimension and characteristics of D-series rings

| | Outer skin portion | | Inner Skin Portion | | Reservoir | |
|---|---|---|---|---|---|---|
| Batch | Placebo Polymer | Thickness (μm) | Granulate E2 | wt % | Thickness (μm) | Granulate ENG | wt % |
| D1 | EVA15 | 33 | D | 18 | 270 | K | 0.41 |
| D2 | EVA15 | 33 | D | 18 | 230 | L | 0.51 |
| D3 | EVA15 | 33 | D | 18 | 155 | L | 0.51 |
| D4 | EVA15 | 33 | D | 18 | 212 | L | 0.51 |
| D5 | EVA15 | 33 | D | 18 | 153 | L | 0.51 |

TABLE $3^e$

Fiber dimensions and characteristics of E-series rings

| | Outer skin portion | | Inner Skin Portion | | Reservoir | |
|---|---|---|---|---|---|---|
| Batch | Placebo Polymer | Thickness (μm) | Granulate E2 | wt % | Thickness (μm) | Granulate ENG | wt % |
| E1 | EVA15 | 24 | D | 18 | 240 | L | 0.51 |
| E2 | EVA15 | 28 | D | 18 | 170 | L | 0.51 |
| E3 | EVA15 | 24 | D | 18 | 141 | L | 0.51 |
| E4 | EVA15 | 24 | D | 18 | 339 | L | 0.51 |
| E5 | EVA15 | 20 | D | 18 | 310 | L | 0.51 |
| E6 | EVA15 | 24 | D | 18 | 240 | L | 0.51 |
| E7 | EVA15 | 28 | D | 18 | 310 | L | 0.51 |
| E8 | EVA15 | 18 | D | 18 | 240 | L | 0.51 |
| E9 | EVA15 | 20 | D | 18 | 170 | L | 0.51 |
| E10 | EVA15 | 30 | D | 18 | 240 | L | 0.51 |
| E11 | EVA15 | 24 | D | 18 | 240 | L | 0.51 |

Assembly Having the Thermal Welding Process Settings of Table $4^a$

All fiber batches listed in Table $3^a$, $3^b$, $3^c$ and $3^e$ were cut to a target length of 157±1 mm using a Metzer-Dracon cutting machine and the resulting pieces were assembled to rings. During assembly the terminal ends of the fiber pieces were welded together using the settings given in Table 4a.

TABLE 4[a]

process settings thermal welding process

| Assembling | Set point |
|---|---|
| Heating time | 8 sec. |
| Welding time | 17 sec. |
| Welding temperature | 130° C. |
| Cooling time | 15 sec. |

Assembly Having the Thermal Welding Process Settings of Table 4[b]

All fiber batches listed in Table 3[d] were cut in-line to a target length of 157±1 mm and the resulting pieces were assembled to rings using a CCM assembly machine. During assembly the terminal ends of the fiber pieces were welded together using the settings given in Table 4[b].

TABLE 4[b]

process setting thermal welding process

| Assembling | Set point |
|---|---|
| Heating time | 8 sec. |
| Welding time | 18-20 sec. |
| Welding temperature | 110-114° C. |
| Cooling time | Time needed to pass 30° C. |

Example 2

In-Vitro Release Rate

The in-vitro release rate of A, B, C, and E-series was determined in 100 ml purified water containing 0.5 wt % sodium lauryl sulfate (SLS) to maintain sink conditions. The in-vitro release rate of the D-series was determined in 250 ml purified water containing 0.5 wt % sodium lauryl sulfate (SLS) to maintain sink conditions. The rings are incubated in the continuously stirred (750 rpm.) in-vitro release medium which is maintained at 37±0.2° C. and refreshed every 24 hours. Detection of the active ingredients in the in-vitro release medium can be performed with HPLC using detectors and under conditions readily identified by the skilled person.

The average day 2-21 release rate is defined as the arithmetic mean of the individual release rates obtained between and including the days 2 and 21. The average day 2-31 is defined analogously.

In-Vitro Release of the a Series

The in-vitro release data obtained on the ring formulation A1 to A15 are provided in Table 5.

TABLE 5

In-vitro release data obtained for E2 and ENG on samples A-series

| | Skin thickness (μm) | | Drug load | In-vitro release E2 (μg/day) | | | In-vitro release ENG (μg/day) | | |
|---|---|---|---|---|---|---|---|---|---|
| Batch | Outer portion | Inner portion | ENG (wt %) | Day 1 | Day 2-21 | Day 31 | Day 1 | Day 2-21 | Day 31 |
| A1 | 100 | 140 | 0.41 | 259 | 122 | 109 | 190 | 86 | 58 |
| A2 | 65 | 340 | 0.31 | 397 | 177 | 151 | 66 | 44 | 34 |
| A3 | 100 | 240 | 0.51 | 303 | 124 | 111 | 138 | 78 | 58 |
| A4 | 30 | 140 | 0.41 | 581 | 307 | 217 | 247 | 112 | 72 |
| A5 | 65 | 240 | 0.41 | 376 | 179 | 152 | 136 | 71 | 52 |
| A6 | 65 | 240 | 0.41 | 372 | 179 | 153 | 136 | 71 | 52 |
| A7 | 100 | 340 | 0.41 | 297 | 124 | 111 | 66 | 50 | 39 |
| A8 | 30 | 240 | 0.31 | 612 | 316 | 224 | 131 | 65 | 46 |
| A9 | 65 | 340 | 0.51 | 382 | 180 | 153 | 96 | 67 | 52 |
| A10 | 65 | 140 | 0.31 | 335 | 178 | 152 | 168 | 74 | 50 |
| A11 | 65 | 240 | 0.41 | 372 | 181 | 154 | 145 | 71 | 52 |
| A12 | 100 | 240 | 0.31 | 288 | 124 | 112 | 96 | 50 | 37 |
| A13 | 65 | 140 | 0.51 | 313 | 177 | 150 | 302 | 117 | 78 |
| A14 | 30 | 240 | 0.51 | 622 | 316 | 223 | 208 | 99 | 71 |
| A15 | 30 | 340 | 0.41 | 581 | 311 | 223 | 139 | 65 | 48 |

From the data in Table 5, it becomes evident that the E2 release is affected by the thickness of the outer portion of the skin, but not by the thickness of the inner portion of the skin. This is in strong contrast to the ENG release rate which is also affected by the inner portion of the skin. The latter becomes evident by comparing release rates obtained on rings with identical skin thickness, the same concentration ENG in the core but different dimensions for the inner portion of the skin. The relevant examples are: A4/A15, A1/A7, A2/A10 and A9/A13.

In FIG. 1 the average ENG in-vitro release rate is plotted against the total skin thickness. The ENG release linearly decreases with increasing total skin thickness. Thus, the skin affects the release of E2 and ENG differently. The release of E2 is affected by the thickness of the depletion layer whereas the release of ENG is affected by the combined thickness of inner and outer skin portion.

In Vitro Release of the B Series

Differentiation of the diffusion length for the dissolved drug in the core and the solid drug in the inner portion of the skin allows independent tuning of the release rate of the drug present in the system. The B series shows that different EVA grades can be used for the inner and outer portion of the skin so long as the VA-content is less than the VA-content of the copolymer used for the core.

The composition and in-vitro release data obtained for E2 and ENG of the B-series is given in Table 6. The EVA grade used for the outer portion of the skin is EVA15 for all samples and the ENG drug load in the core is 0.41 wt. %. The composition of the inner portion of the skin was varied between EVA 15 and EVA 18. The E2 drug load was varied at the levels; 9, 12, 15 and 18 wt. %.

TABLE 6

In-vitro Release Data for E2 and ENG

| Batch | Skin Outer portion μm | Skin Inner portion EVA | Skin Inner portion μm | E2 wt % | In-vitro release E2 (μg/day) Day 1 | In-vitro release E2 (μg/day) Day 2-21 | In-vitro release E2 (μg/day) Day 31 | In-vitro release ENG (μg/day) Day 1 | In-vitro release ENG (μg/day) Day 2-21 | In-vitro release ENG (μg/day) Day 31 |
|---|---|---|---|---|---|---|---|---|---|---|
| B1 | 65 | 15 | 140 | 18 | 365 | 174 | 150 | 237 | 93 | 64 |
| B2 | 65 | 15 | 340 | 18 | 404 | 175 | 152 | 106 | 55 | 43 |
| B3 | 65 | 15 | 140 | 15 | 367 | 168 | 142 | 212 | 95 | 64 |
| B4 | 65 | 15 | 340 | 15 | 440 | 172 | 144 | 77 | 56 | 43 |
| B5 | 65 | 15 | 140 | 12 | 437 | 163 | 133 | 213 | 97 | 65 |
| B6 | 65 | 15 | 340 | 12 | 479 | 167 | 136 | 83 | 58 | 44 |
| B7 | 65 | 15 | 140 | 9 | 559 | 153 | 118 | 236 | 99 | 64 |
| B8 | 65 | 15 | 340 | 9 | 645 | 158 | 123 | 96 | 60 | 44 |
| B9 | 65 | 18 | 140 | 18 | 306 | 177 | 159 | 251 | 111 | 69 |
| B10 | 65 | 18 | 340 | 18 | 324 | 180 | 161 | 96 | 71 | 51 |
| B11 | 65 | 18 | 140 | 15 | 395 | 176 | 155 | 257 | 111 | 68 |
| B12 | 65 | 18 | 340 | 15 | 493 | 179 | 157 | 104 | 71 | 51 |
| B13 | 65 | 18 | 140 | 12 | 472 | 173 | 147 | 266 | 113 | 68 |
| B14 | 65 | 18 | 340 | 12 | 579 | 176 | 150 | 109 | 72 | 51 |
| B15 | 65 | 18 | 140 | 9 | 560 | 167 | 138 | 277 | 114 | 68 |
| B16 | 65 | 18 | 340 | 9 | 825 | 174 | 141 | 125 | 74 | 51 |

The rings in Table 6 have been manufactured with an inner portion varying in thickness. The odd numbers have a thickness of 140 μm and the even numbers have a thickness of 340 μm. By pairwise comparing the E2 release of rings having the same E2 load, the same EVA grade used for the inner portion, but different thicknesses of the inner portion of the skin (B1 with B2; B3 with B4 and so on) it becomes evident that the E2 release is not affected (within 3% margin) by the thickness of the inner portion of the skin. This can be further substantiated by comparing the means of the average day 2-21 E2 release of the odd (B1, B3, B5 and B7) and even (B2, B4, B6 and B8) samples, which are 165 μg/day and 169 μg/day respectively. The release of ENG dissolved in the core of the system however is strongly affected by the thickness of the inner portion of the skin as illustrated by the means of the average release ENG release, which are 96 μg/day and 57 μg/day.

The same procedure of comparing release data of the odd with even samples having a 140 μm and 340 μm thick inner skin portion can be repeated for the samples B9 to B16. The samples B9 to B16 differ from the samples B1 to B8 in that the inner portion of the skin is composed of an EVA copolymer having a VA-content of approximately 3% higher than the EVA grade used for the outer portion, i.e., the depletion layer. The means of the average day 2-21 E2 release are 173 μg/day and 178 μg/day, for the odd (140 μm inner portion) and the even (340 μm) rings, respectively. The means for the ENG release are 113 μg/day and 72 μg/day respectively. Thus, it can be concluded that rings with a skin consisting of an inner and outer portion made of a different EVA grade display the similar behaviour as the system made out of a single EVA copolymer so long as the VA-content of both grades used for the skin is lower than the VA-content used for the core.

Figure 2:
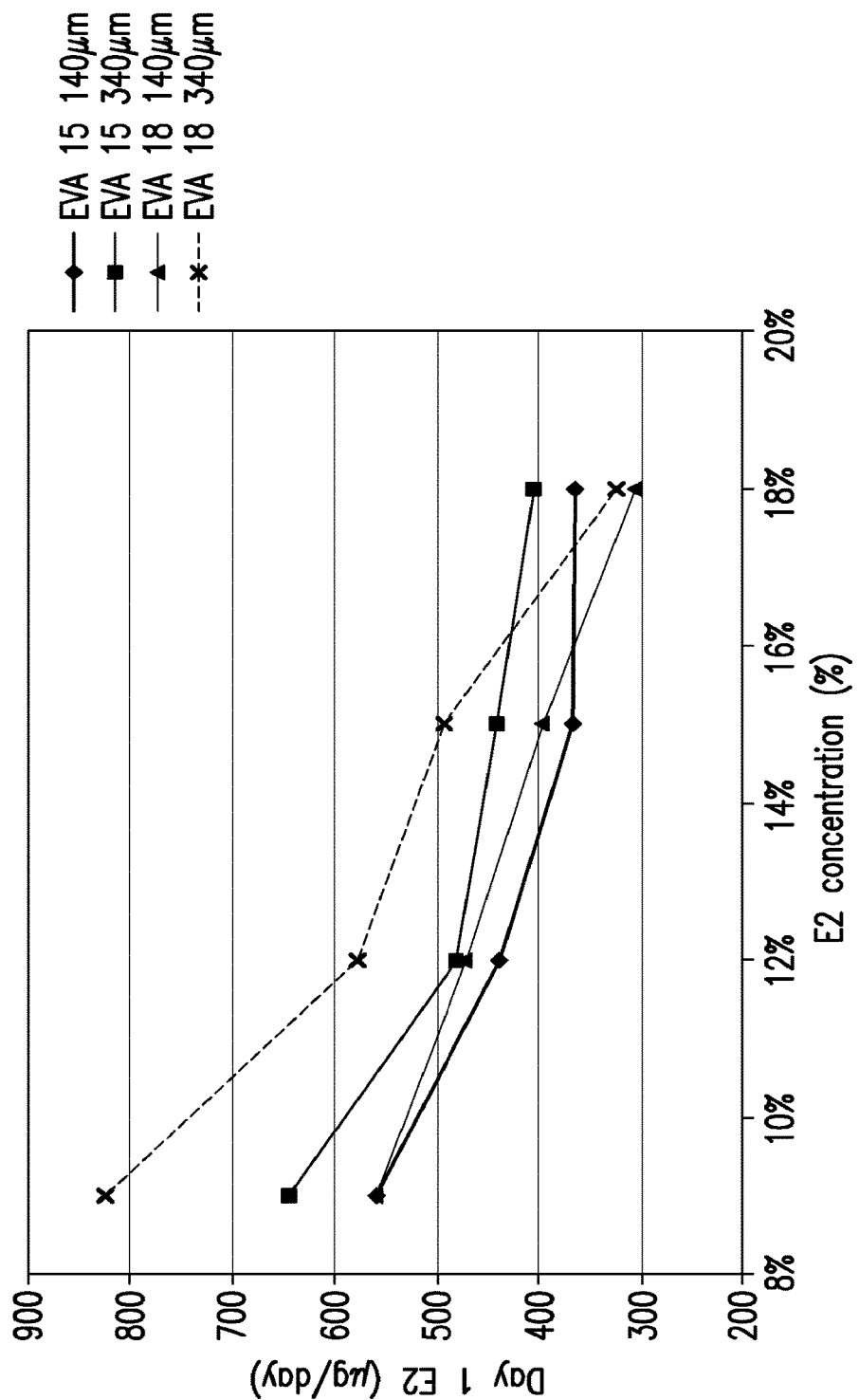
FIG. 2 shows the 17beta-estradiol (E2) day 1 burst release versus the concentration of E2 loaded in the inner skin portion of some of the exemplified embodiments described herein.

By comparing groups of rings with varying E2 drug load, identical thickness of the inner portion of the skin and identical EVA grade used for the inner portion, it appears from the data provided in Table 6 that the E2 day 1 burst release is dependent on the concentration of E2 loaded in the inner skin portion. The effects are graphically presented in FIG. 2.

Not being bound by theory, the inventors believe that this phenomena is caused by the kinetics of recrystallization. A higher drug load will result in a higher concentration of seed crystals, upon which recrystallization can occur when the drug loaded fiber is cooled after co-extrusion. Drug concentrations above 15% wt are preferred because of a lower day-1 burst release.

In Vitro Release of the C Series

The composition, process settings and in-vitro release data obtained for E2 and ENG of the C series is given in Table 7. The EVA grade used for the outer portion of the skin is EVA15 and the thickness was 50 μm for all samples. The ENG drug load in the core is 0.41 wt. %. The E2 load of the inner portion of the skin was varied between 9 and 27 wt. %. The thickness of the inner portion of the skin was varied between 80 and 290 μm. The co-extrusion rate was varied between 2 and 6 m/min and the co-extrusion temperature was varied between 100° and 110° C.

TABLE 7

In-vitro Release Data Obtained for E2 and ENG on Samples C series

| Batch | Rate (m/min) | Temp. (° C.) | [E2] (%) | Inter (μm) | Day 1 E2 (μg/day) | Day 2-24 E2 (μg/day) | Day 1 Eng (μg/day) | Day 2-24 Eng (μg/day) |
|---|---|---|---|---|---|---|---|---|
| C1 | 6 | 110 | 9 | 190 | 351 | 182 | 288 | 94 |
| C2 | 2 | 110 | 9 | 290 | 438 | 180 | 294 | 76 |
| C3 | 4 | 105 | 18 | 240 | 302 | 205 | 191 | 70 |
| C4 | 4 | 105 | 18 | 240 | 303 | 207 | 188 | 70 |
| C5 | 2 | 110 | 27 | 190 | 306 | 211 | 198 | 75 |
| C6 | 6 | 100 | 9 | 290 | 376 | 184 | 292 | 75 |
| C7 | 2 | 100 | 27 | 290 | 305 | 212 | 140 | 56 |
| C8 | 6 | 100 | 27 | 190 | 315 | 221 | 196 | 75 |
| C9 | 2 | 100 | 9 | 190 | 316 | 180 | 283 | 93 |
| C10 | 6 | 110 | 27 | 290 | 320 | 221 | 134 | 59 |

TABLE 7-continued

In-vitro Release Data Obtained for E2 and ENG on Samples C series

| Batch | Rate (m/min) | Temp. (° C.) | [E2] (%) | Inter (μm) | Day 1 E2 (μg/day) | Day 2-24 E2 (μg/day) | Day 1 Eng (μg/day) | Day 2-24 Eng (μg/day) |
|---|---|---|---|---|---|---|---|---|
| C11 | 4 | 105 | 18 | 240 | 309 | 208 | 179 | 71 |
| C12 | 4 | 105 | 18 | 80 | 305 | 210 | 297 | 125 |

Statistical analysis revealed that E2 and ENG IVR were not significantly dependent of co-extrusion rate and co-extrusion temperature. It appears that the E2 day 1 burst release is dependent on the E2 load of the inner portion of the skin. Batches C1, C2, C6 and C9 (9% E2 load) revealed a considerably higher E2 burst release than all other batches loaded with 18 and 27% E2 in the inner portion of the skin. The formulation C12 not belonging to the statistical design was not included in the statistical analysis.

TABLE 8 factorial 2$^{4-1}$ design supplemented with repeated centre points

| Batch | Rate (m/min) | Temp. (° C.) | [E2] (%) | Interm. (μm) | Remark |
|---|---|---|---|---|---|
| C1 | 6 | 110 | 9 | 190 | ½ fraction design |
| C2 | 2 | 110 | 9 | 290 | ½ fraction design |
| C3 | 4 | 105 | 18 | 240 | ½ fraction design (center) |
| C4 | 4 | 105 | 18 | 240 | ½ fraction design (center) |
| C5 | 2 | 110 | 27 | 190 | ½ fraction design |
| C6 | 6 | 100 | 9 | 290 | ½ fraction design |
| C7 | 2 | 100 | 27 | 290 | ½ fraction design |
| C8 | 6 | 100 | 27 | 190 | ½ fraction design |
| C9 | 2 | 100 | 9 | 190 | ½ fraction design |
| C10 | 6 | 110 | 27 | 290 | ½ fraction design |
| C11 | 4 | 105 | 18 | 240 | ½ fraction design (center) |
| C12 | 4 | 105 | 18 | 80 | Extreme test thin intermediate thickness |

In Vitro Release of the D Series

TABLE 9 in-vitro release data obtained for E2 and ENG on samples D-series

| Batch | Thickness inner portion (μm) | Drug load (wt. %) | In-vitro release E2 (μg/day) | | | In-vitro release ENG (μg/day) | | |
|---|---|---|---|---|---|---|---|---|
| | | | Day 1 | Day 2-21 | Day 21 | Day 1 | Day 2-21 | Day 21 |
| D1 | 270 | 0.41 | 647 | 299 | 253 | 160 | 69 | 58 |
| D2 | 230 | 0.51 | 658 | 299 | 237 | 95 | 79 | |
| D3 | 155 | 0.51 | 543 | 295 | 250 | 304 | 123 | 97 |
| D4 | 212 | 0.51 | 566 | 295 | 245 | 236 | 100 | 81 |
| D5 | 153 | 0.51 | 569 | 301 | 249 | 292 | 125 | 98 |

The E2 release of the D-series of ring is governed by an equally thick depletion layer or outer portion of the skin of 33 μm resulting in an equal E2 release for the D-series rings (within 3% error margin). The release of etonogestrel is governed by the thickness of the inner portion of the skin and the amount of ENG loaded in the core of the system.

In Vitro Release of the E Series

TABLE 10 in-vitro release data obtained for E2 and ENG on samples E-series

| Batch | Skin (μm) | Inter (μm) | E2 (μg/day) | | | Eng (μg/day) | | |
|---|---|---|---|---|---|---|---|---|
| | | | Day 1 | Average day 2-21 | Day 21 | Day 1 | Average day 2-21 | Day 21 |
| E1 | 24.0 | 240.0 | 1011 | 365 | 301 | 178 | 94 | 77 |
| E2 | 28.0 | 170.0 | 851 | 338 | 284 | 244 | 119 | 95 |
| E3 | 24.0 | 141.0 | 886 | 358 | 297 | 286 | 136 | 105 |
| E4 | 24.0 | 339.0 | 1007 | 367 | 302 | 122 | 79 | 67 |
| E5 | 20.0 | 310.0 | 1029 | 393 | 315 | 140 | 86 | 71 |
| E6 | 24.0 | 240.0 | 921 | 358 | 298 | 187 | 100 | 82 |
| E7 | 28.0 | 310.0 | 904 | 333 | 286 | 132 | 82 | 69 |
| E8 | 18.3 | 240.0 | 1037 | 401 | 318 | 196 | 103 | 84 |
| E9 | 20.0 | 170.0 | 947 | 382 | 308 | 261 | 126 | 99 |
| E10 | 29.7 | 240.0 | 844 | 319 | 276 | 183 | 97 | 81 |
| E11 | 24.0 | 240.0 | 925 | 354 | 296 | 189 | 99 | 82 |

Figure 3:
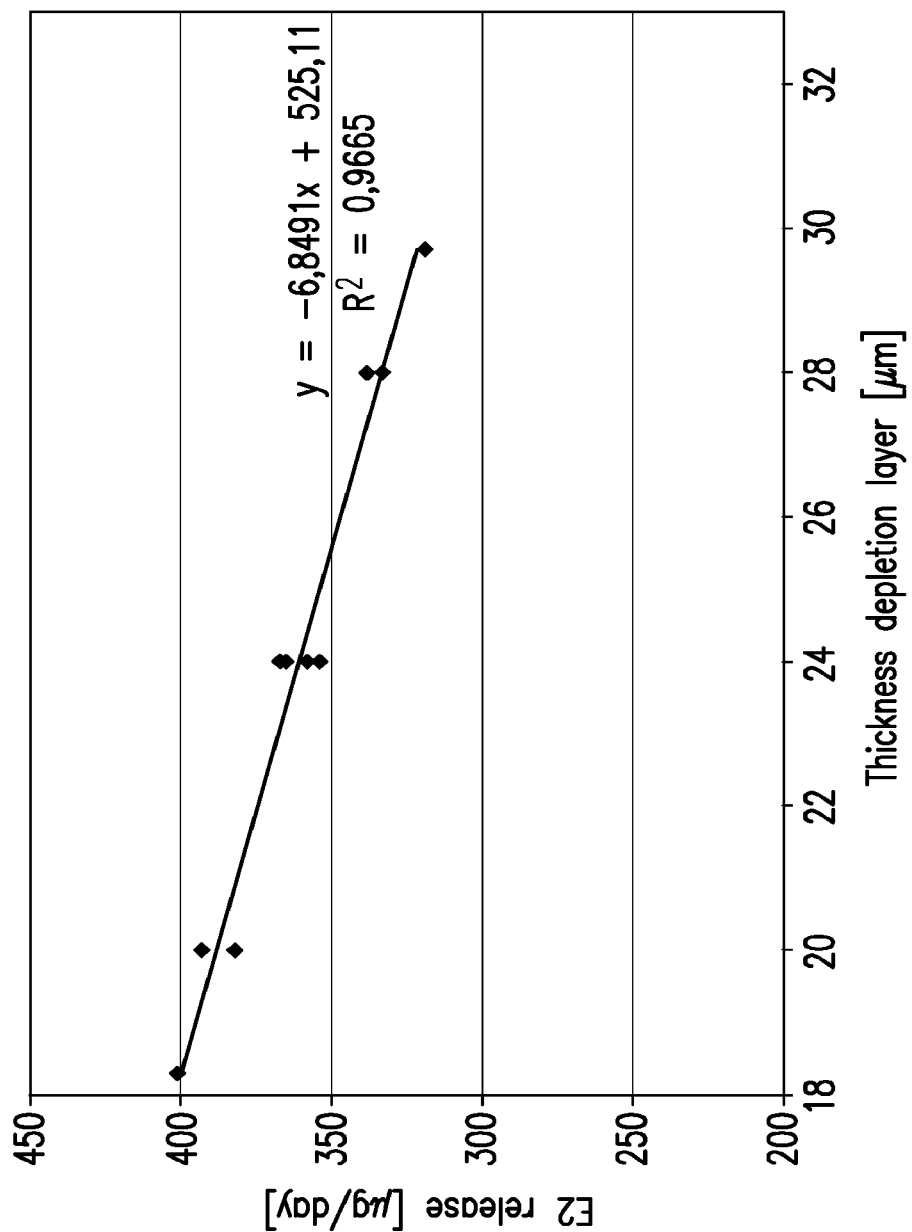
FIG. 3 shows the linear correlation between the thickness of the depletion layer and the E2 average release rate of some of the exemplified embodiments described herein.

In line with observations done on the rings series-A, the E2 release rate of the E series of rings is governed by the thickness of the depletion layer. The graph given in FIG. 3 substantiates the linear correlation between the thickness of the depletion layer and the E2 average release rate.

The ENG release rate however is affected by the inner portion of the skin as well. The latter becomes evident by comparing release rates obtained on rings with identical depletion layer thickness, but different dimensions for the inner portion of the skin. The relevant examples are: E1/E3/E4, E2/E7 and E5/E9.

Figure 4:
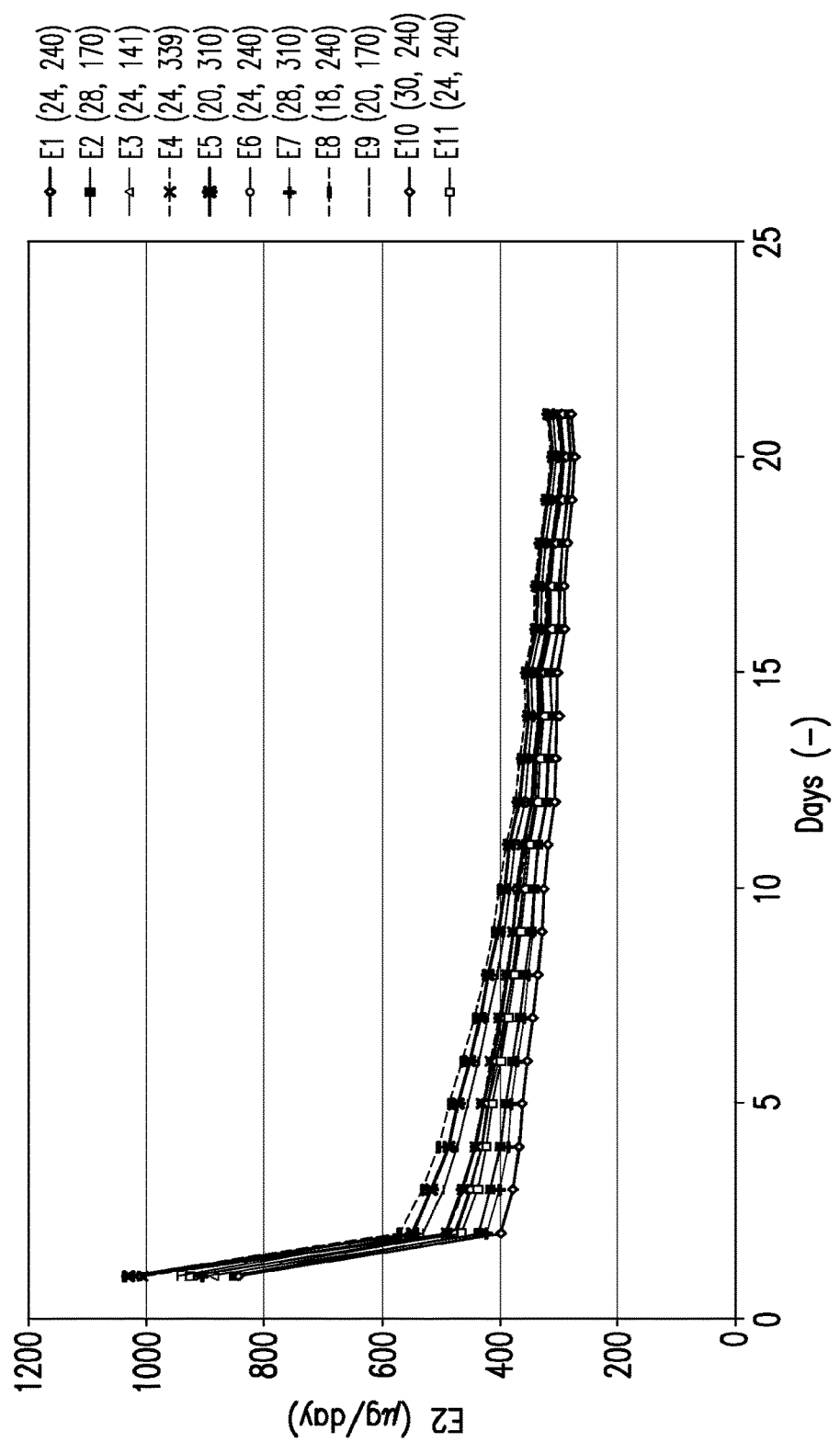
FIG. 4 shows E2 release profiles of some of the exemplified embodiments described herein.
Figure 5:
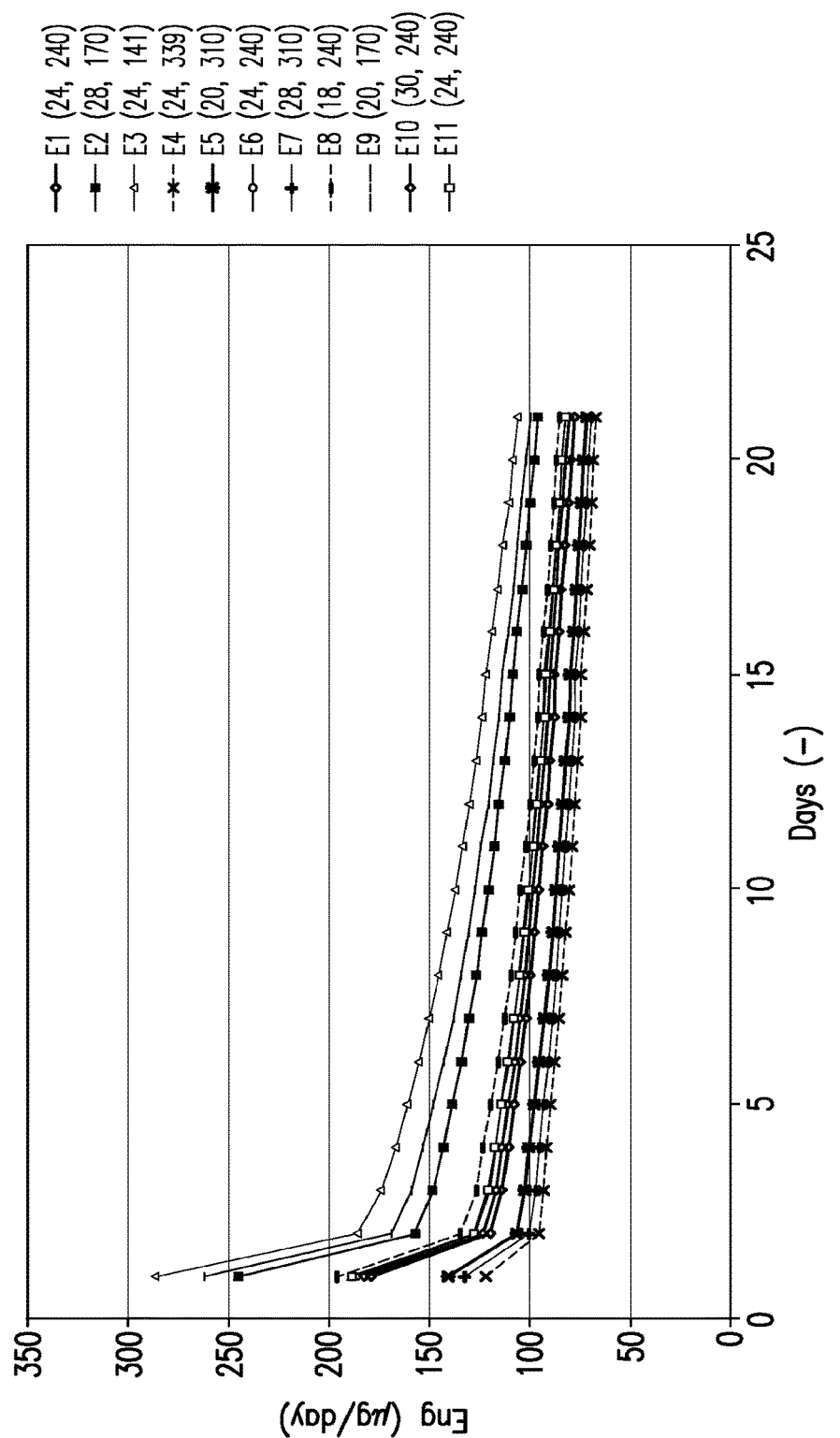
FIG. 5 shows ENG release profiles of some of the exemplified embodiments described herein.

The E2 and ENG release profiles are given in the FIG. 4 and FIG. 5 respectively.

Example 3

Comparative Example

Manufacturing Composition Comprising EE and ENG for Core and an Intermediate Layer (IL)

The manufacturing principles for mixing, tri-coextrusion and welding are similar to the manufacturing principles described in Example 1. Similar equipment and mixing times for powder blending can be used. Furthermore the temperature settings applied for blend-extrusion as well as co-extrusion are in the same range and can be readily identified by the skilled person.

The active granulate composition comprising EE and ENG for core and intermediate layer respectively is given in Table 11. Both actives are incorporated in the EVA28 copolymer with relatively high drug permeability.

TABLE 11 composition ENG and EE medicated granulate in EVA28

| Material | Active granulate N | Active granulate O | Active granulate P |
|---|---|---|---|
| Etonogestrel | 7.0 wt % | 11.0 wt % | |
| Ethinyl Estradiol | | | 0.15 wt % |
| EVA 28 | 92.90 wt % | 88.90 wt % | 99.76 wt % |
| Magnesium stearate | 0.1 wt % | 0.1 wt % | 0.1 wt % |
| Total | 100.0 wt % | 100.0 wt % | 100.0 wt % |

The active granules were further processed to drug loaded fibers, consisting of an EE loaded core, an intermediate layer loaded with crystalline ENG and the latter is covered by a skin. The core and intermediate layer are both made of EVA28 with relatively high drug permeability and the skin is made of EVA9 with relatively low permeability. The composition of the fibers is given in Table 12. The fibers were cut to pieces of 157±1 mm and assembled to rings using the same welding process as described in Example 1.

TABLE 12

| | Skin | | Intermediate Layer | | Core | |
|---|---|---|---|---|---|---|
| Batch | Placebo Polymer | Thickness (μm) | Granulate ENG wt % | | Thickness (μm) | Granulate EE wt % |
| F1 | EVA9 | 94 | O | 11 | 60 | P 0.14 |
| F2 | EVA9 | 94 | N | 7 | 95 | P 0.14 |

The in-vitro release rate was determined in 200 ml purified water under sink conditions. The rings are incubated in the continuously stirred (750 rpm.) in-vitro release medium which is maintained at 37±0.2° C. and refreshed every 24 hours in order to maintain ink conditions. Detection of the concentration of active ingredients in the in-vitro release medium can be performed using UV and fluorescence detection for ENG and EE respectively at wave lengths readily identified by the skilled person. The measurement of the in-vitro release rates was performed in six-fold (n=6) and the averages and ranges are given in Table 13.

TABLE 13 in-vitro release data obtained for ENG and EE

| | Layer thickness (μm) | | In-vitro release ENG (μg/day) | | | In-vitro release EE (μg/day) | | |
|---|---|---|---|---|---|---|---|---|
| Batch | Skin | IL | Day 1 | Day 2-21 | Day 21 | Day 1 | Day 2-21 | Day 21 |
| F1 | 94 | 60 | 160 (152-164) | 114 (112-115) | 107 (106-108) | 22 (22-22) | 14 (14-14) | 13 (13-13) |
| F2 | 94 | 95 | 164 (162-168) | 111 (110-112) | 102 (101-103) | 21 (20-21) | 14 (14-14) | 12 (12-13) |

The crystalline drug in F1 and F2 is loaded in an intermediate layer made out of polymer with high drug permeability relative to the polymer used for the skin. From the in-vitro release results given in Table 13 it becomes evident that the release behaviour is very different from the release behaviour of the ring containing the crystalline drug in the skin. Varying the thickness of the intermediate layer from 60 μm to 95 μm—a more than 50% increase of its thickness—does not affect the release of the dissolved drug (EE) loaded in the core. Apparently the intermediate layer does not contribute effectively to the permeation resistance of the compound loaded in the core.

The release rate of the dissolved drug in this comparative example is not governed by the dimensions of the layer containing the crystalline drug. This in strong contrast to rings containing crystalline drug in the skin.

Example 4

ENG and E2 Permeability of EVA Copolymers

Methods

For the determination of the solubility concentration and diffusion coefficient a method was developed. The method consists in preparing polymer slab composites with one layer highly loaded with active ingredient (60 wt %) on top of a layer of placebo polymer. The two layers were first pressed separately in a hot press and thereafter combined, also using the press, into a two layer structure. The diffusion of the active ingredient from the loaded layer through the placebo layer is measured in time, for the active ingredient/polymer combination adequate analysis method. Thereafter the experimental diffusion data is fitted with a mathematical model based on Fick's $2^{nd}$ law of diffusion in one direction. The differential equation is solved using trigonometrical series with the solubility concentration and diffusion coefficient as only unknown variables.

In the Tables $14^a$ and $14^b$ the experimentally obtained drug-in-polymer diffusivity and solubility and the resulting permeability is given for the active agents ENG and E2.

TABLE $14^a$

Permeability ENG in EVA copolymers

| VA % | Cs mg/g | D ×10$^{-13}$ m$^2$/s | P ×10$^{-12}$ kg/ms |
|---|---|---|---|
| 9 | 0.4 | 2.29 | 0.09 |
| 15 | 0.9 | 3.17 | 0.27 |
| 28 | 3.22 | 4.80 | 1.47 |

TABLE $14^b$

Permeability E2 in EVA copolymers

| VA % | Cs mg/g | D ×10$^{-13}$ m$^2$/s | P ×10$^{-12}$ kg/ms |
|---|---|---|---|
| 15 | 2.31 | 1.38 | 0.30 |
| 19 | 1.98 | 6.47 | 1.22 |
| 28 | 2.77 | 14.50 | 3.82 |
| 33 | 7.39 | 15.72 | 11.04 |

Figure 6:
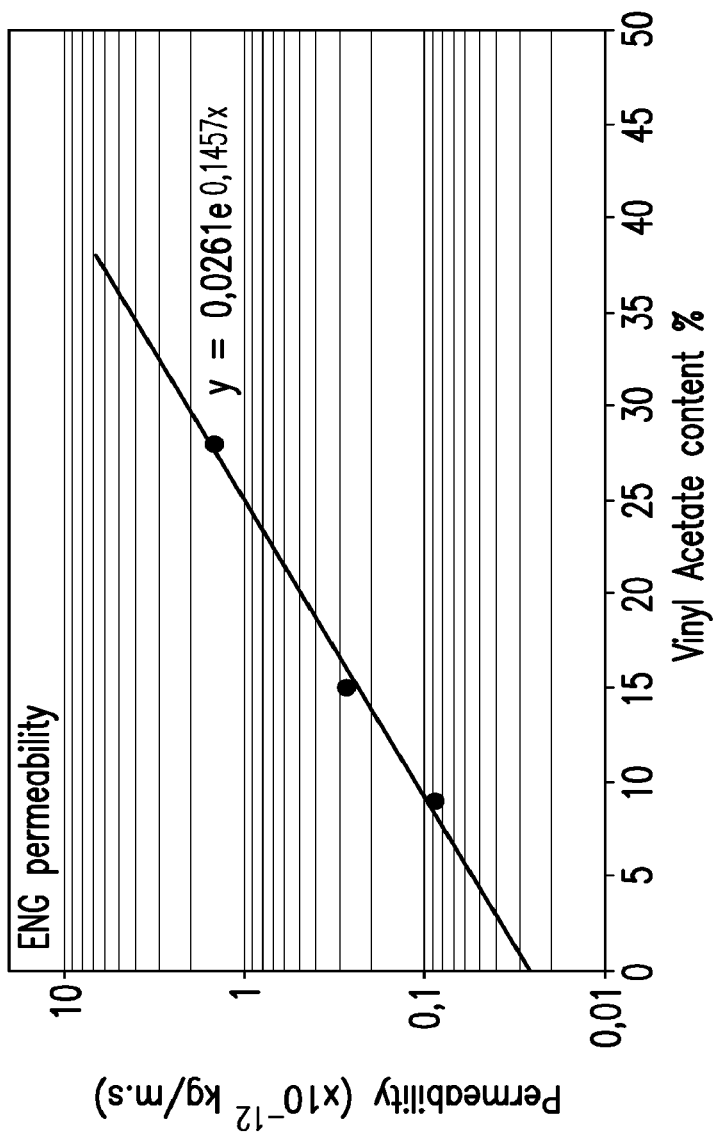
FIG. 6 shows the ENG permeability plotted on a logarithmic scale against the vinylacetate (VA)-content of the ethylene-vinylacetate (EVA) copolymer.
Figure 7:
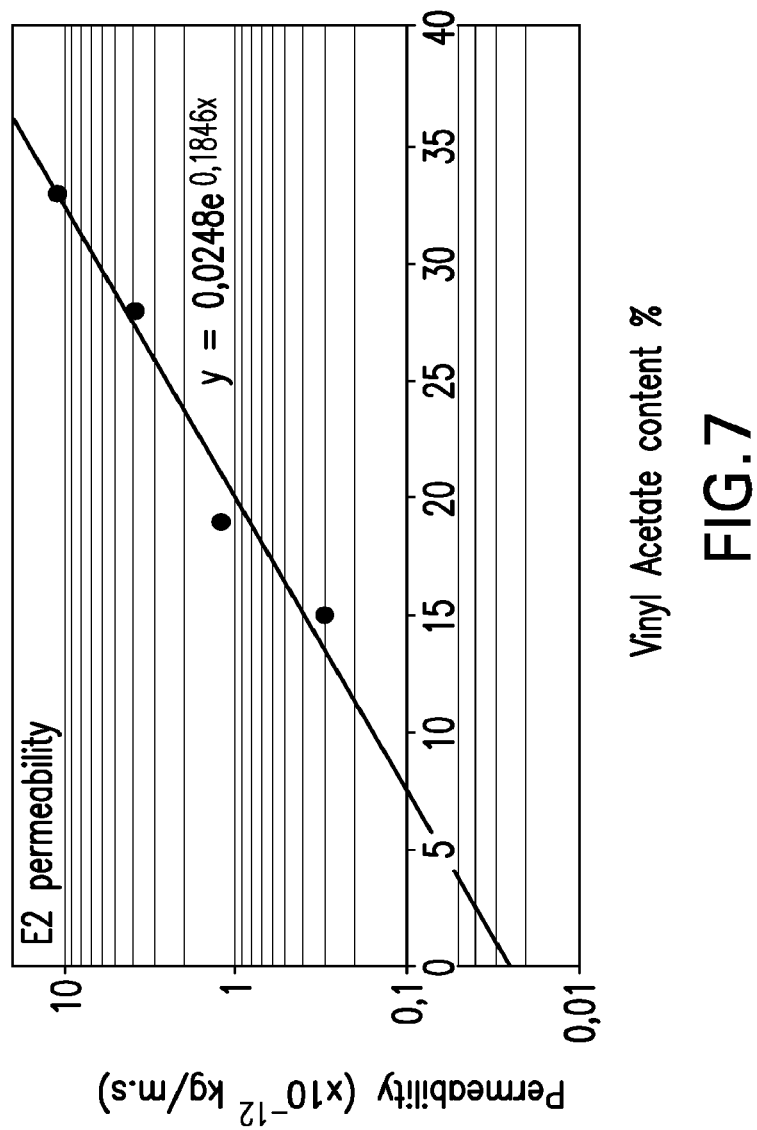
FIG. 7 shows the E2 permeability plotted on a logarithmic scale against the VA-content of the EVA copolymer.

In FIG. 6 and FIG. 7 the ENG and E2 permeability are plotted on a logarithmic scale against the VA-content of the EVA copolymer. The data points can be fitted by the following exponential equation $P \times 10^{-12} = 0.0261 e^{0.1457 \cdot VA\%}$ and $P \times 10^{-12} = 0.0248 e^{0.1846 \cdot VA\%}$ for ENG and E2 respectively. Based on interpolation drug-in-polymer permeability of ENG and E2 in EVA 19 and EVA25 have been calculated.

TABLE 15

Permeability of EVA25 relative to EVA19 for the actives ENG and E2

| VA % | 19 | 25 | Relative permeability $P_{EVA25}:P_{EVA19}$ |
|---|---|---|---|
| P (ENG) ×10$^{-12}$ kg/ms | 0.42 | 1.00 | 2.4 |
| P (E2) ×10−12 kg/ms | 0.83 | 2.50 | 3.0 |

From the drug-in-polymer permeability data provide in Table 15 it can be concluded that the permeability of EVA19 and all grade with a lower VA-content is significantly below the permeability of EVA25 and all grades with a higher VA-content.

Example 5

Evaluation of the Release Kinetics of E2 Loaded in the Skin

The in-vitro release of E2 from the IVR delivery systems D1, D2 and D3 has been compared to the in-vitro release kinetics of the compounds EE and ENG released from NUVARING, which is considered a reservoir system.

For the purpose of adequately comparing the release profiles obtained for the systems D1, D2 and D3 and NUVARING, the release profiles had to be normalized. The latter was done by dividing the individual release rates measured on day-2 until day 21 by the release rate obtained on the second day. The day-1 burst release is governed by not directly related transient phenomena and therefore not considered.

Figure 8:
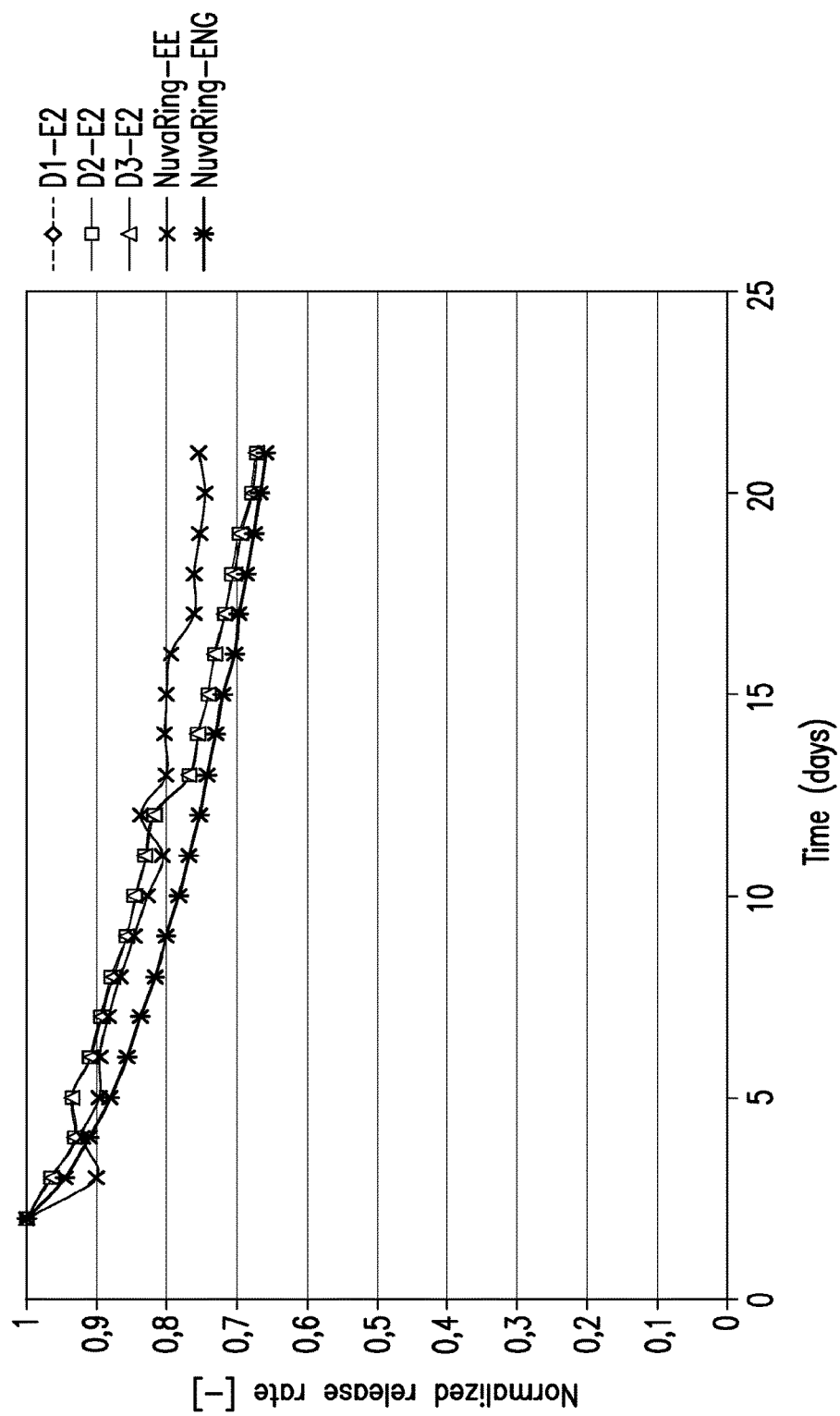
FIG. 8 shows normalized release profiles of some of the exemplified embodiments described herein and NUVARING.

The normalized release profiles are visualized in FIG. 8. From FIG. 8 it becomes evident that the shape of the normalized E2 profiles of D1, D2 and D3 are very similar to the shape of the normalized ENG and EE profiles obtained on NUVARING. Thus it can be concluded that the drug delivery system displays in-vitro release kinetics for the compound loaded in the skin which is comparable to the release kinetics obtained with a reservoir system.

An alternate methodology for analysis of the release kinetics is the use of the semi-empirical model proposed by Korsmeyer et al (Journal of Skin Science, 9 (1981) 211-227).

This model relates drug release exponentially to the elapsed time (t):

$$\frac{M_t}{M_\infty} = k \cdot t^n$$

The term $M_t/M_\infty$ is the fraction cumulatively released at time t, k is a constant incorporating characteristics of the drug-polymer pair and n is the diffusional exponent. This equation was first developed for release of drugs from a plane sheet and the characteristic diffusional coefficients for matrix and zero order release are n=0.5 and n=1, respectively. Subsequent analysis by P. L. Ritger et al (Journal of Controlled Release, 5 (1987) 23-36) revealed that the diffusional coefficient for matrix release from a cylindrical geometry is n=0.45. The diffusional coefficient for time independent release (zero order) remains n=1 and is independent of geometry.

The exponential relation of Korsmeyer can be rewritten as:

$$M_t = M_\infty \cdot k \cdot t^n = k' \cdot t^n \rightarrow \log(M_t) = \log(k') + n \cdot \log(t)$$

Figure 9:
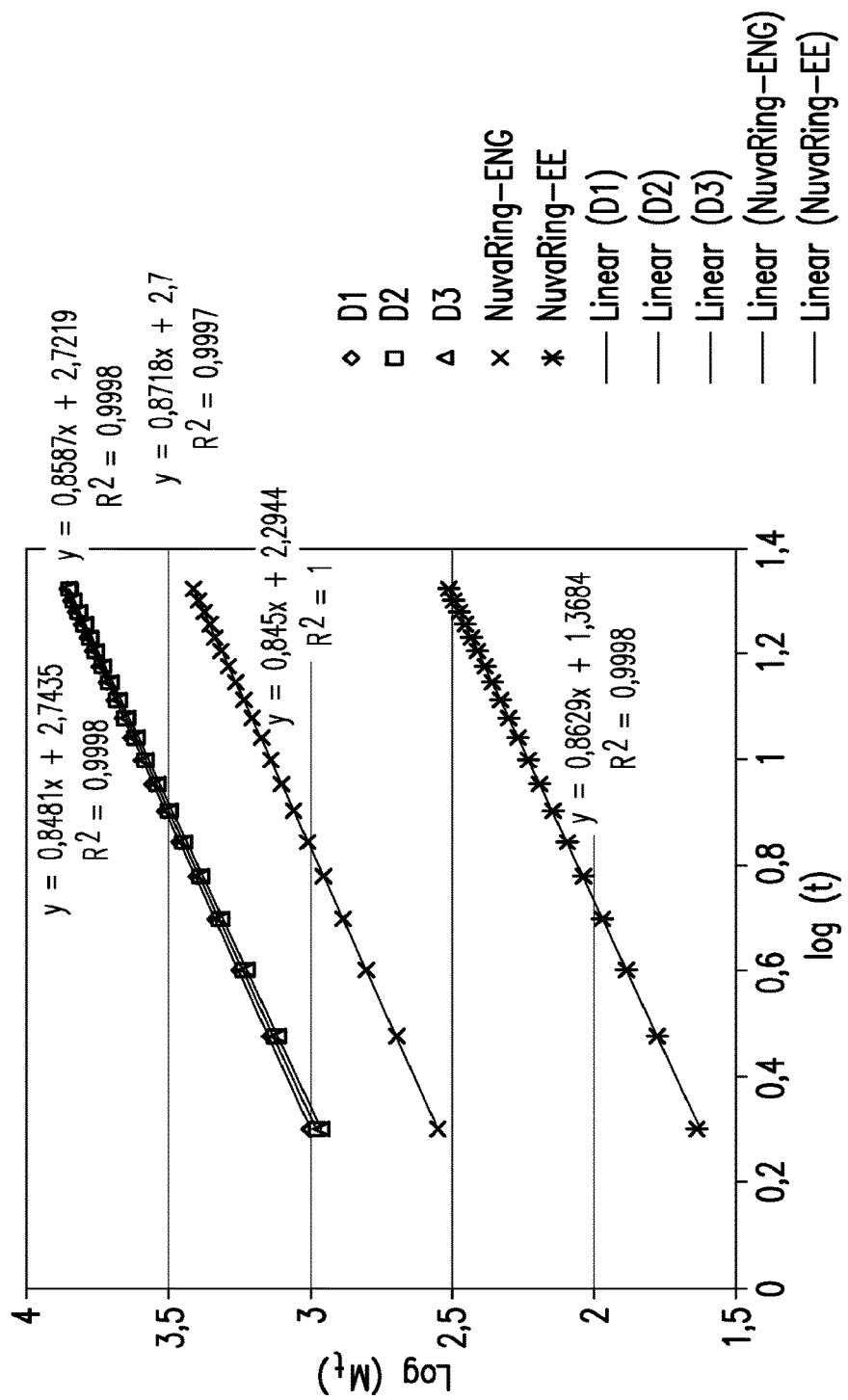
FIG. 9 shows the diffusional exponent of some of the exemplified embodiments described herein and NUVARING determined by plotting log ($M_t$) versus log (t) and fitting of a regression line through the data points

Hence the diffusional exponent can be determined by plotting log ($M_t$) versus log (t) and the subsequent fitting of a regression line through the data points. The regression lines are plotted in FIG. 9 and the diffusional coefficient corresponding with the slope of regression lines are summarized in Table 16.

The diffusional coefficients found for the E2 release are in the same range as the values found for EE and ENG release from NUVARING. Furthermore the correlation coefficient of 1.000 indicates a good fit of the data using the Korsmeyer model.

TABLE 16

Diffusional coefficients

| Batch | Drug | n | $R^2$ |
|---|---|---|---|
| D1 | E2 | 0.85 | 1.000 |
| D2 | E2 | 0.86 | 1.000 |
| D3 | E2 | 0.87 | 1.000 |
| NUVARING | ENG | 0.85 | 1.000 |
|  | EE | 0.86 | 1.000 |

The release kinetics of the drug E2 loaded in the skin displays release kinetics very much akin the pseudo zero-order release kinetics obtained for the ENG and EE released from NUVARING which is considered a reservoir type system. The latter is confirmed by the analysis using the model of Korsmeyer. In the continuum between matrix-type release and perfect zero-order release, represented by values for the diffusional coefficient of n=0.45 and n=1, the obtained diffusional coefficients of n=0.85 to n=0.87 corresponds with a release as a function of time much more akin to zero order release than a matrix type release.

The invention claimed is:

1. An intra-vaginal drug delivery system consisting essentially of i) a core of a first ethylene-vinylacetate copolymer and etonogestrel, wherein the etonogestrel is dissolved in the first ethylene-vinylacetate copolymer, and (ii) a skin surrounding the core of a-second ethylene-vinylacetate copolymer, wherein the second ethylene-vinylacetate copolymer is the only polymer in the skin, and wherein the first ethylene-vinylacetate copolymer has a higher vinylacetate content than the second ethylene-vinylacetate copolymer, and wherein 17beta-estradiol is loaded in the skin in solid form, such that a depletion layer is preformed, and upon release the 17beta-estradiol loaded in the skin displays a near zero order release profile.

2. The drug delivery system according to claim 1, wherein the 17beta-estradiol is 17beta-estradiol hemi-hydrate.

3. The drug delivery system according to claim 1, wherein the first thermoplastic polymer is ethylene-vinylacetate copolymer having a vinylacetate content between 25-40% vinylacetate.

4. The drug delivery system according to claim 1, wherein the first thermoplastic polymer is ethylene-vinylacetate copolymer having a vinylacetate content between 25-33% vinylacetate.

5. The drug delivery system according to claim 1, wherein the first thermoplastic polymer is ethylene-vinylacetate copolymer having a vinylacetate content of 28% vinylacetate.

6. (The drug delivery system according to claim 1, wherein the second thermoplastic polymer is ethylene-vinylacetate copolymer having a vinylacetate content between 9-19% vinylacetate.

7. The drug delivery system according to claim 1, wherein the second thermoplastic polymer is ethylene-vinylacetate copolymer having a vinylacetate content between 9-18% vinylacetate.

8. The drug delivery system according to claim 1, wherein the second thermoplastic polymer is ethylene-vinylacetate copolymer having a vinylacetate content of 15% vinylacetate.

\* \* \* \* \*